United States Patent
Pressly et al.

(10) Patent No.: US 12,214,225 B2
(45) Date of Patent: *Feb. 4, 2025

(54) METHODS FOR FIXING HAIR AND SKIN

(71) Applicant: OLAPLEX, INC., Santa Barbara, CA (US)

(72) Inventors: Eric D. Pressly, Santa Barbara, CA (US); Craig J. Hawker, Santa Barbara, CA (US)

(73) Assignee: OLAPLEX, INC., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/811,158

(22) Filed: Aug. 21, 2024

(65) Prior Publication Data

US 2024/0408419 A1 Dec. 12, 2024

Related U.S. Application Data

(63) Continuation of application No. 18/177,011, filed on Mar. 1, 2023, which is a continuation of application No. 17/941,675, filed on Sep. 9, 2022, which is a continuation of application No. 16/830,789, filed on Mar. 26, 2020, now Pat. No. 11,446,525, which is a continuation of application No. 15/854,504, filed on Dec. 26, 2017, now Pat. No. 10,639,505, which is a continuation of application No. 14/835,223, filed on Aug. 25, 2015, now Pat. No. 9,855,447, which is a continuation of application No. 14/748,831, filed on Jun. 24, 2015, now Pat. No. 9,144,537, which is a continuation of application No. 14/459,012, filed on Aug. 13, 2014, now Pat. No. 9,095,518, which is a (Continued)

(51) Int. Cl.
| | |
|---|---|
| *A61K 8/45* | (2006.01) |
| *A61K 8/02* | (2006.01) |
| *A61K 8/22* | (2006.01) |
| *A61K 8/36* | (2006.01) |
| *A61K 8/362* | (2006.01) |
| *A61K 8/365* | (2006.01) |
| *A61K 8/40* | (2006.01) |
| *A61K 8/41* | (2006.01) |
| *A61K 8/44* | (2006.01) |
| *A61K 8/46* | (2006.01) |
| *A61Q 5/00* | (2006.01) |
| *A61Q 5/02* | (2006.01) |
| *A61Q 5/04* | (2006.01) |
| *A61Q 5/08* | (2006.01) |
| *A61Q 5/10* | (2006.01) |
| *A61Q 5/12* | (2006.01) |
| *A61Q 19/00* | (2006.01) |

(52) U.S. Cl.
CPC ............ *A61Q 5/12* (2013.01); *A61K 8/0204* (2013.01); *A61K 8/0216* (2013.01); *A61K 8/22* (2013.01); *A61K 8/36* (2013.01); *A61K 8/362* (2013.01); *A61K 8/365* (2013.01); *A61K 8/40* (2013.01); *A61K 8/41* (2013.01); *A61K 8/447* (2013.01); *A61K 8/45* (2013.01); *A61K 8/46* (2013.01); *A61Q 5/002* (2013.01); *A61Q 5/004* (2013.01); *A61Q 5/02* (2013.01); *A61Q 5/04* (2013.01); *A61Q 5/08* (2013.01); *A61Q 5/10* (2013.01); *A61Q 19/007* (2013.01); *A61K 2800/42* (2013.01); *A61K 2800/596* (2013.01); *A61K 2800/70* (2013.01); *A61K 2800/884* (2013.01); *A61K 2800/94* (2013.01)

(58) Field of Classification Search
None
See application file for complete search history.

(56) References Cited

U.S. PATENT DOCUMENTS

| | | | |
|---|---|---|---|
| 2,850,351 A | 9/1958 | Moore et al. | |
| 3,142,623 A | 7/1964 | Zviak et al. | |

(Continued)

FOREIGN PATENT DOCUMENTS

| | | |
|---|---|---|
| CN | 1334718 | 2/2002 |
| CN | 105431128 | 3/2016 |

(Continued)

OTHER PUBLICATIONS

Softer Hair <https://softerhair.com/the-importance-of-using-a-ph-balanced-shampoo/>; Jul. 12, 2019. (Year: 2019).*

(Continued)

*Primary Examiner* — Nicole P Babson
(74) *Attorney, Agent, or Firm* — NORTON ROSE FULBRIGHT US LLP

(57) ABSTRACT

A method of treating keratin of a person is disclosed. The method includes contacting the keratin with a composition comprising a compound having a chemical structure of

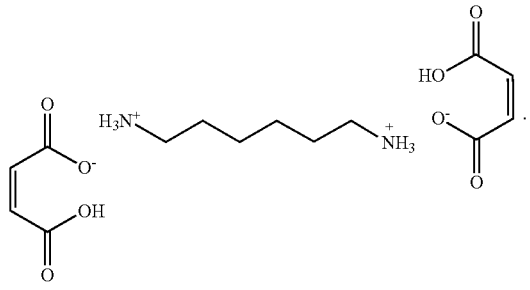

17 Claims, No Drawings

Related U.S. Application Data continuation-in-part of application No. PCT/US2014/049388, filed on Aug. 1, 2014, which is a continuation-in-part of application No. 14/257,076, filed on Apr. 21, 2014, now abandoned, and a continuation-in-part of application No. 14/257,089, filed on Apr. 21, 2014, now abandoned, and a continuation-in-part of application No. 14/257,056, filed on Apr. 21, 2014, now abandoned.

(60) Provisional application No. 62/000,340, filed on May 19, 2014, provisional application No. 61/903,239, filed on Nov. 12, 2013, provisional application No. 61/885,898, filed on Oct. 2, 2013, provisional application No. 61/867,872, filed on Aug. 20, 2013, provisional application No. 61/861,281, filed on Aug. 1, 2013.

(56) References Cited

U.S. PATENT DOCUMENTS

| | | |
|---|---|---|
| 3,472,243 A | 10/1969 | Wall et al. |
| 3,568,685 A | 3/1971 | Scott |
| 3,840,656 A | 10/1974 | Kalopissis et al. |
| 4,007,143 A | 2/1977 | Lyndon et al. |
| 4,067,345 A | 1/1978 | Kelly et al. |
| 4,138,478 A | 2/1979 | Reese et al. |
| 4,240,450 A | 12/1980 | Grollier et al. |
| 4,425,132 A | 1/1984 | Grollier et al. |
| 4,532,950 A | 8/1985 | Lang et al. |
| 4,567,039 A | 1/1986 | Stadnick et al. |
| 4,658,839 A | 4/1987 | Dallal et al. |
| 4,793,993 A | 12/1988 | Siuta-Mangano et al. |
| 4,812,307 A | 3/1989 | Siuta-Mangano et al. |
| 4,834,971 A | 5/1989 | Klenk et al. |
| 5,143,518 A | 9/1992 | Madrange et al. |
| 5,200,429 A | 4/1993 | Sato et al. |
| 5,221,286 A | 6/1993 | Singleton et al. |
| 5,350,572 A | 9/1994 | Savaides et al. |
| 5,356,438 A | 10/1994 | Kim et al. |
| 5,490,980 A | 2/1996 | Richardson et al. |
| 5,565,216 A | 10/1996 | Cowsar et al. |
| 5,651,960 A | 7/1997 | Chan et al. |
| 5,656,265 A | 8/1997 | Bailey et al. |
| 5,811,085 A | 9/1998 | Halloran |
| 5,833,966 A | 11/1998 | Samain |
| 6,010,690 A | 1/2000 | Varco |
| 6,173,717 B1 | 1/2001 | Schonert et al. |
| 6,358,502 B1 | 3/2002 | Tanabe et al. |
| 6,458,906 B1 | 10/2002 | Torgerson et al. |
| 6,537,532 B1 | 3/2003 | Torgerson et al. |
| 6,572,663 B1 | 6/2003 | Pitfield et al. |
| 6,706,258 B1 | 3/2004 | Gallagher et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,179,302 B2 | 2/2007 | Boswell et al. |
| 7,390,479 B2 | 6/2008 | Sockel et al. |
| 7,597,880 B2 | 10/2009 | Darkwa et al. |
| 7,598,213 B2 | 10/2009 | Geary et al. |
| 8,137,414 B2 | 3/2012 | Wood et al. |
| 8,298,519 B2 | 10/2012 | Adams et al. |
| 8,343,238 B1 | 1/2013 | Lopez et al. |
| 8,556,992 B2 | 10/2013 | De George et al. |
| 8,613,913 B2 | 12/2013 | Chang et al. |
| 9,095,518 B2 | 8/2015 | Pressly et al. |
| 9,144,537 B1 | 9/2015 | Pressly et al. |
| 9,180,086 B2 | 11/2015 | Cabourg et al. |
| 9,326,926 B2 | 5/2016 | Pressly et al. |
| 9,498,419 B2 | 11/2016 | Pressly et al. |
| 9,597,273 B2 | 3/2017 | Pressly et al. |
| 9,668,954 B2 | 6/2017 | Pressly et al. |
| 9,713,583 B1 | 7/2017 | Pressly et al. |
| 9,717,668 B2 | 8/2017 | Pressly et al. |
| 9,855,447 B2 | 1/2018 | Pressly et al. |
| 9,872,821 B1 | 1/2018 | Pressly et al. |
| 10,076,475 B2 | 9/2018 | Gershon et al. |
| 10,076,478 B2 | 9/2018 | Pressly et al. |
| 10,639,505 B2 | 5/2020 | Pressly et al. |
| 10,792,233 B2 | 10/2020 | Pressly et al. |
| 11,191,707 B2 | 12/2021 | Pressly et al. |
| 11,446,525 B2 | 9/2022 | Pressly |
| 2001/0042276 A1 | 11/2001 | Kawasoe et al. |
| 2002/0189034 A1 | 12/2002 | Kitabata et al. |
| 2002/0197227 A1 | 12/2002 | Scholz |
| 2003/0037384 A1 | 2/2003 | Ngyuen et al. |
| 2003/0049222 A1 | 3/2003 | Akhter et al. |
| 2003/0072962 A1 | 4/2003 | Matsuzaki et al. |
| 2004/0034944 A1 | 2/2004 | Legrand et al. |
| 2004/0034946 A1 | 2/2004 | Legrand et al. |
| 2004/0086475 A1 | 5/2004 | Boswell et al. |
| 2004/0088800 A1 | 5/2004 | Cotteret |
| 2004/0166073 A1 | 8/2004 | Darkwa et al. |
| 2005/0036970 A1 | 2/2005 | Sabbagh et al. |
| 2005/0087718 A1 | 4/2005 | Okada et al. |
| 2005/0193501 A1 | 9/2005 | Chan et al. |
| 2005/0215622 A1 | 9/2005 | Majeed et al. |
| 2006/0024257 A1 | 2/2006 | Chang et al. |
| 2006/0228316 A1 | 10/2006 | Cannell et al. |
| 2007/0041921 A1 | 2/2007 | Neill et al. |
| 2007/0067924 A1 | 3/2007 | Beck et al. |
| 2007/0141005 A1 | 6/2007 | Wood et al. |
| 2007/0261594 A1 | 11/2007 | Vaskelis et al. |
| 2007/0264208 A1 | 11/2007 | Mougin et al. |
| 2008/0066773 A1 | 3/2008 | Anderson et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2009/0022681 A1 | 1/2009 | Carballada et al. |
| 2009/0126756 A1 | 5/2009 | Syed et al. |
| 2009/0252697 A1 | 10/2009 | Barbarat et al. |
| 2010/0004391 A1 | 1/2010 | Haddleton et al. |
| 2010/0015253 A1 | 1/2010 | Benjamin |
| 2010/0202998 A1 | 8/2010 | Ramos-Stanbury et al. |
| 2011/0038818 A1 | 2/2011 | Onyebuagu et al. |
| 2011/0097293 A1 | 4/2011 | Grey et al. |
| 2011/0250153 A1 | 10/2011 | Owen et al. |
| 2011/0256084 A1 | 10/2011 | Dixon et al. |
| 2012/0024309 A1 | 2/2012 | Pratt et al. |
| 2012/0114584 A1 | 5/2012 | Woghiren et al. |
| 2012/0145477 A1 | 6/2012 | Peaslee |
| 2012/0148517 A1 | 6/2012 | Gilmore et al. |
| 2012/0180807 A1 | 7/2012 | Flohr |
| 2012/0225106 A1 | 9/2012 | Ross et al. |
| 2012/0244082 A1 | 9/2012 | Sulzbach et al. |
| 2013/0034515 A1 | 2/2013 | Stone et al. |
| 2013/0078205 A1 | 3/2013 | Dayan |
| 2013/0152959 A1 | 6/2013 | Genain et al. |
| 2013/0172518 A1 | 7/2013 | Huang et al. |
| 2013/0309190 A1 | 11/2013 | Dimotakis et al. |
| 2013/0340785 A1 | 12/2013 | Baum et al. |
| 2014/0125452 A1 | 5/2014 | Josefiak et al. |
| 2014/0186283 A1 | 7/2014 | Cabourg et al. |
| 2014/0196741 A1 | 7/2014 | Cabourg et al. |
| 2015/0034117 A1 | 2/2015 | Pressly et al. |
| 2015/0034119 A1 | 2/2015 | Pressly et al. |
| 2015/0174023 A1 | 6/2015 | Washington et al. |
| 2015/0297496 A1 | 10/2015 | Kroon et al. |
| 2015/0320658 A1 | 11/2015 | Flohr et al. |
| 2015/0328102 A1 | 11/2015 | Pressly et al. |
| 2016/0081899 A1 | 3/2016 | Pressly et al. |
| 2016/0193129 A1 | 7/2016 | Pressly et al. |
| 2016/0263003 A1 | 9/2016 | Pressly et al. |
| 2016/0310394 A1 | 10/2016 | Pressly et al. |
| 2020/0009035 A1 | 1/2020 | Pressly et al. |
| 2022/0218579 A1 | 7/2022 | Pressly |
| 2023/0010188 A1 | 1/2023 | Pressly |

FOREIGN PATENT DOCUMENTS

| | | |
|---|---|---|
| CN | 105640790 | 6/2016 |
| DE | 1220969 | 7/1966 |
| DE | 4300320 | 7/1994 |

(56) References Cited

FOREIGN PATENT DOCUMENTS

| | | |
|---|---|---|
| DE | 10051773 | 4/2002 |
| DE | 10051774 | 4/2002 |
| DE | 102004052480 | 5/2006 |
| DE | 202015104742 | 10/2015 |
| EC | 993171 | 10/1999 |
| EC | 055712 | 3/2005 |
| EP | 0299764 | 1/1989 |
| EP | 0298684 | 4/1993 |
| EP | 0609796 | 8/1994 |
| EP | 0978272 | 2/2000 |
| EP | 1174112 | 1/2002 |
| EP | 1726289 | 11/2006 |
| EP | 1779896 | 5/2007 |
| EP | 2295029 | 3/2011 |
| EP | 2478892 | 7/2012 |
| FR | 1356138 | 3/1964 |
| FR | 1356139 | 3/1964 |
| FR | 2975900 | 12/2012 |
| GB | 713675 | 8/1954 |
| GB | 741307 | 11/1955 |
| GB | 773559 | 4/1957 |
| GB | 1125794 | 8/1968 |
| GB | 1260451 | 1/1972 |
| GB | 1584364 | 2/1981 |
| JP | H02138110 | 5/1990 |
| JP | 2006045223 | 2/2006 |
| JP | 2006327994 | 12/2006 |
| JP | 2007045802 | 2/2007 |
| JP | 2008162905 | 7/2008 |
| JP | 2009007283 | 1/2009 |
| JP | 2009120563 | 6/2009 |
| JP | 2010155823 | 7/2010 |
| KR | 830002888 | 12/1983 |
| KR | 20010039848 | 7/2001 |
| KR | 1020030003970 | 1/2003 |
| KR | 20040098688 | 11/2004 |
| KR | 1020060059564 | 6/2006 |
| WO | WO1993000882 | 1/1993 |
| WO | WO1993008787 | 5/1993 |
| WO | WO1995000107 | 1/1995 |
| WO | WO1995001152 | 1/1995 |
| WO | WO1997024106 | 7/1997 |
| WO | WO2000032158 | 6/2000 |
| WO | WO2001047486 | 7/2001 |
| WO | WO2002032383 | 4/2002 |
| WO | WO2002032386 | 4/2002 |
| WO | WO2002074272 | 9/2002 |
| WO | WO2006011771 | 2/2006 |
| WO | WO2006051287 | 5/2006 |
| WO | WO2008072672 | 6/2008 |
| WO | WO2009024936 | 2/2009 |
| WO | WO2010049434 | 5/2010 |
| WO | WO2011134785 | 11/2011 |
| WO | WO2012084532 | 1/2012 |
| WO | WO2012164064 | 1/2012 |
| WO | WO2012080321 | 6/2012 |
| WO | WO2012122457 | 9/2012 |
| WO | WO2012164065 | 12/2012 |
| WO | WO2014016407 | 1/2014 |
| WO | WO2014118212 | 8/2014 |
| WO | WO2014125452 | 8/2014 |
| WO | WO2014167508 | 10/2014 |
| WO | WO2014207097 | 12/2014 |
| WO | WO2015017768 | 2/2015 |
| WO | WO2015026994 | 2/2015 |
| WO | WO2015175986 | 11/2015 |
| WO | WO2016207840 | 12/2016 |
| WO | WO2017041908 | 3/2017 |

OTHER PUBLICATIONS

"ThatBlondeGirl Mandie"—Youtube video: Brunette Goes Blonde No Damage, No. 1, retrieved online from, <https://www.youtube.com/watch?v=7flFBmxJk8s> (Jan. 11, 2015), retrieved Dec. 13, 2022.
"ThatBlondeGirl Mandie"—Youtube video: Olaplex Platinum Blonde, No. 2, retrieved online from, <https://www.youtube.com/watch?v=JNGFi8vYeMY>. (Jan. 20, 2015), retrieved Dec. 13, 2022.
"ThatBlondeGirl Mandie"—Youtube video: Olaplex Tutorial, No. 3, retrieved online, <https://www.youtube.com/watch?v=kixyDdMf9n4>. (Dec. 30, 2014), retrieved Dec. 13, 2022.
2019Heo3618 appeal of Korean Patent Cancellation Defendant-Inventor Reference Brief (with English Translation) filed Nov. 12, 2020.
2019Heo3618 Appeal of Korean Patent Cancellation Defendant-Intervenor Reference Brief (with English translation) filed Nov. 16, 2020.
2019Heo3618 Appeal of Korean Patent Cancellation, Defendant-Intervenor Presentation (with English translation) dated Sep. 23, 2020.
2019Heo3618 Appeal of Korean Patent Cancellation, Defendant-Intervenor Reference Brief (with English translation) filed Oct. 27, 2020.
2019Heo3618 Appeal of Korean Patent Cancellation, Expert Declaration of Dr. Steve Rannard signed Dec. 25, 2019.
2019Heo3618 Appeal of Korean Patent Cancellation, Expert Declaration of Dr. Steve Rannard signed Jun. 9, 2020.
2019Heo3618 Appeal of Korean Patent Cancellation, Expert Declaration of Dr. Steve Rannard signed Nov. 4, 2020.
2019Heo3618 Appeal of Korean Patent Cancellation, KIPO Defendant Brief (with English translation) dated Sep. 18, 2020.
2019Heo3618 Appeal of Korean Patent Cancellation, KIPO Defendant Presentation (with English Translation) dated Sep. 23, 2020.
2019Heo3618 Korean Court Decision (with English Translation) dated Feb. 3, 2021.
Amazon.com Joico Vero K Pak Veroxide Developer Cream 32 ounce Beauty, filed Jan. 29, 2019.
Amended Statement of Case on Validity (Olaplex) Redacted Version filed Nov. 6, 2017.
Aparecida Da Franca, et al., "Types of Hair Dye and Their Mechanisms of Action", Cosmetics, 2:110-126 (2015).
Asquith, et al., Chemistry of Natural Protein Fibers (1977).
Australian Examination Report Examination Report AU2015058904 mailed Nov. 2, 2016.
B(l)ack to blonde article, behindthechair.com accessed Jan. 1, 2019.
Barradas, et al., "The hydrolysis of maleimide in alkaline solution", Can. J. Chem, 54, 1400-1404 (1976).
Berth and Reese, "Veranderung des haarkeratins durch kosmetische behandlung und naturliche umwelteinflusse", J Soc Cos Chem., 15:659-66 (1964).
Bolduc, C. et al., "Hair Care Products: Waving, Straightening, Conditioning, and Coloring" Clinics in Dermatology 19:431-436 (2001).
Borish Declaration—Redacted version of Exhibit 2025, dated Oct. 20, 2017 (Exhibit 2049) filed in PGR 2017-00012.
Borish, Edward T.—Declaration, signed Oct. 18, 2017 (Redacted, non-confidential version).
Borish, Edward T.—Deposition transcript, pp. 1-204, Jan. 5, 2018.
Borish, Edward T. CV filed Nov. 16, 2018.
Bouillon and Wilkinson, Chapter 1, "Hair Structure, Function, and Physicochemical Properties" in The Science of Hair Care, (2005).
Bouillon and Wilkinson, Chapter 12, "Evaluation of Product Efficacy" in The Science of Hair Care, (2005).
Brief English Summary of Office Action IL (Israel) Application No. 265590 mailed Sep. 23, 2020.
Brown and Pohl, "Permanent Hair Dyes", Society of Cosmetic Chemists, 1-41, (1996).
Brown, Excerpts from the 5th Edition of Organic Chemistry, (2011).
Brown, Hair Coloring, Clairol, Inc., Stamford, Connecticut (1997).
Canadian Office Action 2,947,303 mailed Dec. 28, 2016.
Canadian Protest Application 2,947,303 mailed Feb. 8, 2017.
Canari, "Effect of pH on Dicarboxylic Acids Extraction by Amine-Based Extractants", Ind. Eng. Chem. Res., 42:1293-1300 (2003).
Catzy Blonde Statement of the use of Maleic Acid, dated Dec. 1, 2017.

(56) References Cited

OTHER PUBLICATIONS

Catzy Blonde translation filed Feb. 2, 2018.
Central Role Presentation, dated Jan. 26, 2015.
Certified English Translation of DE 1220969 dated Dec. 13, 2016.
Certified English Translation of KR2006-0059564 dated Dec. 30, 2016.
Chan, "Nucleophile-Initiated Thiol-Michael Reactions: Effect of Organocatalyst, Thiol, and Ene", Macromolecule, 13:6381-6388 (2010).
Christal, Dean—Declaration, signed Oct. 18, 2017(Redacted) filed in PGR 2017-00012.
Chromastics, "The evolution of hair color", Technical ad training manual, pp. 1-32 (2009).
CIR Safety Report "Final Report on the Safety Assessment of Maleic Acid", International Journal of Toxicology, 26 (Suppl.2); 125-131, (2007).
Citraconic Acid, C5H604-PubChem, accessed Dec. 21, 2018.
Claims of GB1605346.4 submitted on Sep. 7, 2018.
Combined Search and Examination Report for GB 1523109.5 mailed Feb. 4, 2016.
Combined Search and Examination Report GB 1513932.2 mailed Sep. 24, 2015.
Combined Search and Examination Report GB 1618423.6 mailed Nov. 29, 2016.
Corbett, et al., "Hair Colorants: Chemistry and toxicology", Cosmetic Science Monographs, (1998).
CTFA Cosmetic Ingredient handbook, pp. 1023-1 thru 1023-8, John Wenninger Editor, (1992).
Davies and Evans, "The isomerization of maleic acid in aqueous solutions", Transections of Faraday Society, 52:74-80 (1956).
Davis, et al., Excerpts from Modern Chemistry, pp. 214,215, and 454 (1999).
Declaration by Dr. Hefford dated Jan. 7, 2020 filed in KR Appeal No. 2019Heo3618.
Declaration by Prof. Steve Rannard dated Dec. 25, 2019 filed in KR Appeal No. 2019Heo3618.
Declaration of Arun Nandagiri dated Jan. 30, 2017, with curriculum vitae.
Declaration of Arun Nandagiri dated Jan. 31, 2017, with curriculum vitae.
Declaration of Dr. Robert J.W. Hefford filed in Application No. AU2017251818 signed Jul. 27, 2020.
Declaration of Dr. Robert J.W. Hefford filed in Application No. EP3142637 signed Apr. 10, 2020.
Declaration of Dr. Steve Rannard filed in Application No. AU2017251818 signed Dec. 9, 2020.
Declaration of Dr. Steve Rannard filed in Application No. AU2017251818 signed Nov. 9, 2020.
Declaration of Edward T. Borish in Support of Olaplex's Motion for a Preliminary Injunction, filed Jan. 18, 2017, with curriculum vitae.
Declaration of Hiroshi J. Sheraton filed in Application No. AU2017251818 signed Jul. 28, 2020.
Declaration of Hiroshi J. Sheraton filed in Application No. EP3142637 signed Jul. 8, 2020.
Declaration of Prof. Steve Rannard dated Oct. 27, 2019 filed in EP 15725209.9.
Declaration of Robert Vernon Law filed in Application No. AU2017251818 signed Jul. 20, 2020.
Defendant-Intervenor brief in Appeal No. 2019Heo3618, KR (Korea) 1787310, dated Oct. 23, 2019.
Defendant's Brief—Redacted version—in Opposition to Plaintiff's Motion for Preliminary Injunction, by L'Oreal USA Products, Inc., et al., filed in Liqwd, Inc. et al. v. L'Oreal USA, Inc. et al., U.S. District Court for the District of Delaware, Civil Action No. 1:17-cv-00014 on Apr. 17, 2017.
Dispenza License status webpage, https://aca.licensecenter.ny.gov/aca/GeneralProperty/LicenseeDetail, retrieved from the internet Dec. 12, 2017.
Dispenza, Thomas—Declaration, signed Oct. 17, 2017 filed in PGR 2017-00012.
Dispenza, Thomas—Deposition transcript, pp. 1-125, Dec. 13, 2017.
Dmuchovsky, et al., "The Mechanism of the Base-Catalyzed Addition of Thiols to Maleic Anhydride", Free-Radical Addition of Thiols to Maleic Anhydride, 86:2875-2877 (1964).
Doering, et al., "Super mild oxidation coloring: preventing hair damage at the molecular lever", IFSCC Magazine, 10(4):323-9 (2007).
Dombrink and Tanis "pH & hair shampoo," Chem Matters, 8 (1983).
E-mail correspondence regarding documentary evidence as provided by the third party (EX 36), filed May 16, 2018.
Engel, et al., "Fumaric acid production by fermentation", App Microbial Biotechnol, 78:379-89 (2008).
English Summary of Examination Report CN (China) 201480042200.1, dated Jan. 29, 2020.
English Summary of Examination Report QA (Qatar) QA/201601/00021, dated Dec. 12, 2019.
English Summary of IL (Israel) Application No. 265590 dated Mar. 13, 2020.
English Summary of MY (Malaysia) Application No. PI 2016704186 Office Action dated Oct. 26, 2020.
English Summary of Notice of Re-examination CN (China) Application No. 201580026038.9 dated Nov. 25, 2020.
English Summary of Office Action HN (Honduras) 2016002313, dated Feb. 11, 2020.
English Summary of Office Action ID (Indonesia) POD 201608726, dated Oct. 17, 2019.
English Summary of Office Action IL 248989 (with Third Party Submission) mailed Sep. 6, 2017.
English Summary of Office Action MX (Mexico) MX/a/2016/014917, dated Feb. 25, 2020.
English Translation of 2019Heo3618 Appeal of Korean Patent Cancellation, Defendant-Inventor Brief dated Sep. 16, 2020.
English Translation of Defendant-Intervenor brief in Appeal No. 2019Heo3618, KR (Korea) 1787310, dated Oct. 23, 2019.
English Translation of Examination Report PE (Peru) 0001022016/DIN, dated Jan. 15, 2020.
English Translation of KIPO Response Correction in Appeal No. 2019Heo3618, KR (Korea) 1787310, dated Oct. 22, 2019.
English Translation of KIPO Response in Appeal No. 2019Heo3618, KR (Korea) 1787310 dated Oct. 15, 2019.
English Translation of MX (Mexico) Application No. MX/a/2020/011029 Office Action dated Sep. 24, 2021.
English Translation of Packaging in Mintel Database, Record ID 743114, Catzy Hair Colourant, Published Jul. 2007. Translation Filed Feb. 2, 2018.
English Translation of PE (Peruvian) Office Action Application No. 002238-2016/DIN dated Sep. 7, 2020.
English Translation of PE (Peruvian) Office Action Application No. 002238-2016/DIN dated Feb. 19, 2021.
English Translation of Third Party Observation BR (Brazil) Application No. 1120160263782 dated Mar. 17, 2020.
English Translation of VN (Vietnam) Application No. 1-2016-04522 Office Action dated Sep. 9, 2021.
Evans, "Fatigue testing of hair—A statistical approach to hair breakage", J Cosmet. Sci., 60:599-616 (2009).
Evans, et al., "A statistical analysis of hair breakage. II. Repeated grooming experiments", J. Cosmet. Sci., 61:440-455 (2010).
EX 1048, PGR 2018-00025, Public version of Ex 1036, Laboratory Notebook, filed Oct. 10, 2018.
EX 1063, Signori, "FTIR investigation of the damage produced on human hair by weathering and bleaching processes: implementation of different sampling techniques and data processing", International Journal of Cosmetic Science, (1997).
EX 1065, Practical Modern Hair, Science, Chapter 4, (2012).
EX 2003—Liqwd V. L'Oreal 2018 WL480759 (Fed.Cir 2018).
EX 2004—Trial Testimony in Liqwd, Inc. et al. V. L'Oreal (UK) Ltd. et al., EQHC Patents Court, Claim No. HP-2016-000056, Apr. 26, 2018.
EX 2010, pGR 2018-00023, Joico Bleach Powder label with instructions and ingredients, filed May 21, 2018.

(56) References Cited

OTHER PUBLICATIONS

Ex 2011, PGR 2018-00023, Clairol Professional Basic White Powder Lightener label with instructions and ingredients filed May 21, 2018.
EX 2024, PGR 2018-00023, Matrix Light Master Bleach Powder label and instructions, filed May 21, 2018.
EX 2025, PGR 2018-00023, Redken Flash Lift Lightening Power label and instructions, filed May 21, 2018.
EX 2026, PGR 2018-00023, Redken Up to 7 Bleach Powder, label and instructions, filed May 21, 2018.
EX 2027, PGR 2018-00023, L'Oreal Quick Blue Bleach Powder label and instructions, filed May 21, 2018.
Ex 2034—Felthouse, et al., "Maleic Anhydride, Maleic Acid, And Fumaric Acid",—Kirk-0thmer Encyclopedia Of Chemical Technology (First Published Oct. 18, 2001).
Ex 2036—Maleic Acid Safety Data Sheet Vertellus 2011.
Ex 2043—Excerpt From Youtube Video Entitled "How Does Smartbond Technology Work?" By L'Oreal Professionnel, Available At Https://Youtu.Be/Lmyb5fiel1g?T=31 (Visited Oct. 18, 2018).
Ex 2044—Redken Ph-Bonder Technical Guide—Aug. 2016.
EX 2045, PGR 2018-00025, Matrix Bond Ultim8 Techniques Guide, filed Nov. 16, 2018.
EX 2047, PGR 2018-00025, Matrix Bond Ultim8 bottle instructions, filed Nov. 16, 2018.
EX 2048, pGR 2018-00025, Matrix Bond Ultim8 package instructions, filed Nov. 16, 2018.
EX 2049, PGR 2018-00025, Lab report from Analyze Inc., filed Nov. 16, 2018.
EX 2050, PGR 2018-00025, Redken pH Bonder bottle instructions, filed Nov. 16, 2018.
EX 2051, PGR 2018-00025, Redken pH Bonder package instructions, filed Nov. 16, 2018.
EX 2052, PGR 2018-00025, L'Oreal Professional Smartbond bottle instructions, filed Nov. 16, 2018.
EX 2053, PGR 2018-00025, L'Oreal Professional Smartbond package instructions, filed Nov. 16, 2018.
Ex 2055—Wolfram, "The Reactivity Of Human Hair. A Review", Hair Research, (1981).
Ex 2056—Dubief, et al., Chpt. 4 "Hair Care Products", The Science Of Hair Care, Bouillon C, Wilkinson, J. Eds., 2nd Ed. (2005).
Ex 2058—Types Of Professional Haircolor Services (Redken), Https:Www.Redken.Com/Haircolor/Types-Of-Professional-Haircolor-Services (Obtained Jun. 2, 2018).
Ex 2060—Corbett, "The Chemistry Of Hair-Care Products", J. Soc'y Of Dyers And Colourists, 92(8):285-303 (1976).
Ex 2063—Harris, Chpt. 9, "Monoprotic Acid-Base Equilibira", The Science Of Hair Care, Bouillon C, Wilkinson J, Eds., 2d Ed., (2005).
Ex 2066—Harris, Chpt. 10, "Polyprotic Acid-Base Equilibria", Quantitative Chemical Analysis, 7th Ed., (2007).
Ex 2073—(PGR 2018-00025)—Redacted Declaration Of Dean Christal, Dated Oct. 31, 2018.
Ex 2074—(PGR 2018-00025)—Redacted Declaration Of Edward T. Borish, Phd Dated Nov. 16, 2018.
EX 2075, PGR 2018-00025, Redacted LIQWD Inc. Patent Owner Response under 37 CFR 42.220, dated Nov. 16, 2018.
Examination Report GB1513932.2 mailed Sep. 26, 2016.
Examination Report GB1605346.4 mailed Jan. 11, 2017.
Examination Report PH (Philippines) 1-2016-500132, dated Oct. 29, 2019.
Examination report regarding GB (Great Britain) 1605346.4, dated Nov. 13, 2018.
Examination report regarding GB (Great Britain) 1813313.2, dated Jan. 14, 2019.
Expert Village, Hair color mixing and aopplication techniques: Mixing bleach for highlights, https://www.youtube.com/watch?v=nOE_BaC57mw, 3 pages, retrieved from the internet May 17, 2016.
Extended European Search Report EP (Europe) Application No. 20178358.6 dated Jan. 13, 2021.
Facebook page, https://www.facebook.com/behindthechair/photo/a.153398501906.116563.44389181906/10152417864161907/?type=3&theater, May 13, 2014.
Facebook page, https://www.facebook.com/GuyTangHairArtist/photos/a.254923251198058.69129.214382105252173/762062380484140/?type=3&theater, Apr. 17, 2014a.
Facebook page, https://www.facebook.com/GuyTangHairArtist/photos/a.254923251198058.69129.214382105252173/762551773768534/?type=3&theater, Apr. 17, 2014b.
Facebook page, https://www.facebook.com/GuyTangHairArtist/photos/a.254923251198058.69129.214382105252173/767530266604018/?type=3&theater, Apr. 26, 2014.
Facebook page, https://www.facebook.com/GuyTangHairArtist/photos/a.254923251198058.69129.214382105252173/772484942775217/?type=3&theater, May 7, 2014.
Facebook page, https://www.facebook.com/olaplex/photos/a.541423639298984.1073741828.347578558683494/574713415970006/?type=3&theater, Apr. 11, 2014.
Facebook page, https://www.facebook.com/traceycunninghamcolor/posts/10202245158143314, Mar. 9, 2014.
Facebook page, https://www.facebook.com/olaplex/573114059463275, Apr. 7, 2014.
Facebook page, https://www.facebook.com/traceycunninghamcolor/posts/10152466366701095, May 11, 2014.
Fed Cir. decision in Appeal No. 2018-2152, Oct. 17, 2019.
Fibreplex No. 1 Bond Booster, Icare, accessed Oct. 11, 2017.
Fibreplex No. 1 Label, 6 pages, accessed Feb. 28, 2018.
Fibreplex Safety Date Sheet, 5 pages, issued Mar. 16, 2016.
FMC Webinar—The Science of Persulfate Activation, Apr. 24, 2013.
Fragrance Journal, 49-56 (Jan. 1997).
Fueghelman, et al., "Morphology and Properties of Hair", Hair and Hair Care: Cosmetic Science and Technology Series, 17(1): 1-15 (1997).
Gamez-Garcia, et al., "Patterns of Light Interference", Journal of Cosmetic Science, 58(4):269-282 (2007).
Gamez-Garcia, et al., "Understanding Properties of Hair Cuticle", Journal of Cosmetic Science, 423-424 (2006).
Gobbo, et al., "Improved Methodology for the Preparation of Water-Soluble, Maleimide-Functionalized Small Gold Nanoparticles", Langmuir, ACS Publications, 28:12357-12363 (2012).
Grounds of Invalidity filed by L'Oreal (UK) Limited, et al., on Nov. 4, 2016.
Guy Tang on Instagram page, https://www.instagram.com/p/nPmHn7mnA6/ Apr. 26, 2014.
Haake, et al., "Hair breakage—How to measure and counteract", J. Cosmet. Sci., 60:143-151 (2009).
Haddleton CV Jan. 2, 2018.
Haddleton report dated Feb. 2, 2018 (Redacted).
Haddleton report dated Mar. 29, 2018 (Redacted).
Haddleton report, dated Apr. 24, 2018.
Halal "The Chemistry of Haircolor," Slide 36, http://chemistrysimplified.com/wp-content/uploads/2015/07/CEA-2015-Chemistry-of-Haircolor.pdf (2015).
Halal, Hair Structure and Chemistry Simplified, 322 pages (2009).
Hall and Wolfram, "Application of the theory of hydrophobic bonds to hair treatments," J Soc Cosmet Chem., 28:231-41 (1977).
Hefferd Declaration Part 1 of 3—Redacted—filed in *Liqwd, Inc. et al. v. L'Oreal USA, Inc. et al.*, U.S. District Court for the District of Delaware, Civil Action No. 1:17-cv-00014—Apr. 17, 2017.
Hefferd Declaration Part 2 of 3—Redacted—filed in *Liqwd, Inc. et al. v. L'Oreal USA, Inc. et. al.*, U.S. District Court for the District of Delaware, Civil Action No. 1:17-cv-00014—Apr. 17, 2017.
Hefferd Declaration Part 3 of 3—Redacted—filed in *Liqwd, Inc. et al. v. L'Oreal USA, Inc. et. al.*, U.S. District Court for the District of Delaware, Civil Action No. 1:17-cv-00014—Apr. 17, 2017.
Hefford, Robert—report, dated Apr. 25, 2018.
Hefford, Robert—report, dated Feb. 2, 2018.
Hefford, Robert—report, dated Mar. 29, 2018.
Hierarchical Structure, https://www.upload.wikimedia.org/wikipedoa/commons/thumb/5/55/Hierarchical_structure, retrieved from the internet Sep. 22, 2016.

(56) References Cited

OTHER PUBLICATIONS

HiMedia Labs, http://www.himedialabs.com/TD/AT068.pdf, downloaded on Mar. 6, 2018, pp. 1-2, (2011).
Hoshowski, "Conditioning of Hair", Hair and Hair Care, 17(4):65-104 (1997).
Hoyle, et al., "Thiol-click chemistry: a multifaceted toolbox for small molecule and polymer synthesis", Chemical Society Reviews, 39:1355-1387 (2010).
Imai, et al., "The Dyeing Mechanism of Oxidative Hair Color in White and Black Human Hair", J. Soc. Cosmet. Chem. Jpn., 44 (3):208-215 (2010) with English Abstract.
INCi listing ingredient BIS Aminopropyl Diglycol Dimaleate Cosmetics Cosing EC Regulation v2, Mar. 29, 2018.
International Search Report and Written Opinion for PCT/US2015/031166 mailed Jan. 22, 2016.
International Search Report and Written Opinion for PCT application, PCT/US2015/065032, mailed May 9, 2016.
International Search Report and Written Opinion for PCT/US2014/049388 mailed Oct. 29, 2014.
International Search Report and Written Opinion for PCT/US2016/029215 mailed Jul. 8, 2016.
International Search Report and Written Opinion for PCT/US2016/058432, mailed Jan. 16, 2017.
Isaacman, "Just Click It: New Chemical Reactions for Cosmetic Applications", Cosmetics & Toiletries, https://www.cosmeticsandtoiletries.com/research/techtransfer/premium-Just-Click-It-New-Chemical-Reactions-for-Cosmetic-Applications-209714931.html, accessed Apr. 5, 2018.
Jachowicz, "Hair damage and attempts to its repair". J Soc Cosmet Chem., 38:263-86 (1987).
Jankowksa, et al., "The Relations Between Ionic and Non-Ionic Diffusion of Sulfonamides Across the Rabbit Cornea", Investigative Ophthalmology & Visual Science, 27(1):29-37 (1986).
Japan Cosmetic Industry Association ed., 1st Ed., Japan Cosmetic Industry Association, 139-142 with English Summary (2012).
Japanese Office Action for JP 2016-515948 mailed Jan. 25, 2017 (with English Translation).
Japanese Office Action for JP 2016-515948 mailed Jul. 29, 2016 (with English Translation).
John Corbett, Hair Colorants: Chemistry and Toxicology 1-54 (1998).
Joico Verolight Dust-Free Lightening Powder Sleek Shop accessed Mar. 28, 2018.
Joico Verolight Powder Bleach and Verolight Plus MSDS dated Feb. 10, 2013.
Joko, et al., "A Tentative Mechanism of Oxidative Dyeing for Keratin Fibers", J. Soc. Cosmet. Chem. Jpn., 42 (3):185-200 with English Abstract (2008).
JP 2016572832 Pre-Appeal Examination report, Mar. 28, 2019 in English.
Kade, et al., "The Power of Thiol-ene Chemistry", J. Polymer Science Part A: Polym. Chem., 48:743-750 (2010).
Kamath and Robbins, "Hair breakage by combing and brushing—A comment on: T.A. Evans and K. Park, A statistical analysis of hair breakage. II Repeated grooming experiments", J. Cosmet. Sci., 41:439-56 (2010).
Kang, "Hair Dyeing and Hair Damage According to the Number of Dyeing", Master's Thesis, Kwangju Women's University, 11-13 (2006) with English Translation.
Keshouhin kagaku guide [Cosmetic Science Guide] 2nd edition, Fragrance Journal Ltd., May 16, 2011, p. 256-257 with English description.
KIPO Brief in Appeal of Cancellation Decision with English Translation dated Jan. 13, 2020.
Kirschenbaum, et al., "Oxygen radicals from photoirradiated human hair: An ESR and fluorescence study", J Cosmetic Sci., 51:169-182 (2000).
Kline, htt://homepage.smc.edu/kline_peggy/Organic/Amino_Acid_pKa.pdf, obtained online on Mar. 6, 2019, p. 1 (2006).
Kolb, et al., "Click Chemistry: Diverse Chemical Function from a Few Good Reactions", Agnew. Chem. Int. Ed., 40:2004-2021 (2001).
Koval, "Reactions of Thiols," Russian J Organic Chemistry, 43(3):319-49 (2007).
KR 10-1787310 Decision on Cancellation Mar. 5, 2019 (English Translation).
KR 20030003970—Certified English Translation Jan. 14, 2003 LG Household & Health Care, Ltd.
*L'Oreal* vs. *Olaplex* Judgement UK 2019 EWCA CIV 1943, dated Nov. 18, 2019.
L'Oreal Invalidity Opinion Ex A01, filed Jul. 26, 2018.
L'Oreal Invalidity Opinion Ex A02, filed Jul. 26, 2018.
L'Oreal Invalidity Opinion Ex A03, filed Jul. 26, 2018.
L'Oreal Invalidity Opinion Ex A04, filed Jul. 26, 2018.
L'Oreal Invalidity Opinion Ex ADS, filed Jul. 26, 2018.
L'Oreal Invalidity Opinion Ex A06, filed Jul. 26, 2018.
L'Oreal Invalidity Opinion Ex AO?, filed Jul. 26, 2018.
L'Oreal Invalidity Opinion Ex A08, filed Jul. 26, 2018.
L'Oreal Invalidity Opinion Ex A09, filed Jul. 26, 2018.
L'Oreal Invalidity Opinion Ex A10, filed Jul. 26, 2018.
L'Oreal Invalidity Opinion Ex A11, filed Jul. 26, 2018.
L'Oreal Invalidity Opinion Ex A12, filed Jul. 26, 2018.
L'Oreal Invalidity Opinion Ex A13, filed Jul. 26, 2018.
L'Oreal Invalidity Opinion Ex A14, filed Jul. 26, 2018.
L'Oreal Invalidity Opinion Ex A15, filed Jul. 26, 2018.
L'Oreal Invalidity Opinion Ex A16, filed Jul. 26, 2018.
L'Oreal Invalidity Opinion Ex A17, filed Jul. 26, 2018.
L'Oreal Invalidity Opinion Ex A18, filed Jul. 26, 2018.
L'Oreal Invalidity Opinion Ex A19, filed Jul. 26, 2018.
L'Oreal Invalidity Opinion Ex A20, filed Jul. 26, 2018.
L'Oreal Invalidity Opinion Ex A21, filed Jul. 26, 2018.
L'Oreal Invalidity Opinion Ex A22, filed Jul. 26, 2018.
L'Oreal Invalidity Opinion Ex A23, filed Jul. 26, 2018.
L'Oreal Invalidity Opinion Ex A24, filed Jul. 26, 2018.
L'Oreal Invalidity Opinion Ex A25, filed Jul. 26, 2018.
L'Oreal Invalidity Opinion Ex A26, filed Jul. 26, 2018.
L'Oreal Invalidity Opinion Ex A27, filed Jul. 26, 2018.
L'Oreal Invalidity Opinion Ex A28, filed Jul. 26, 2018.
L'Oreal Invalidity Opinion Ex A29, filed Jul. 26, 2018.
L'Oreal Invalidity Opinion Ex A30, filed Jul. 26, 2018.
L'Oreal Invalidity Opinion Ex A31, filed Jul. 26, 2018.
L'Oreal Invalidity Opinion Ex A32, filed Jul. 26, 2018.
L'Oreal Invalidity Opinion Ex A33, filed Jul. 26, 2018.
L'Oreal Invalidity Opinion Ex A34, filed Jul. 26, 2018.
L'Oreal Invalidity Opinion Ex A35, filed Jul. 26, 2018.
L'Oreal Invalidity Opinion Ex A36, filed Jul. 26, 2018.
L'Oreal Invalidity Opinion Ex A37, filed Jul. 26, 2018.
L'Oreal Invalidity Opinion Ex A38, filed Jul. 26, 2018.
L'Oreal Invalidity Opinion Ex A39, filed Jul. 26, 2018.
L'Oreal Invalidity Opinion Ex A40, filed Jul. 26, 2018.
L'Oreal Invalidity Opinion Ex A41, filed Jul. 26, 2018.
L'Oreal Invalidity Opinion Ex A42, filed Jul. 26, 2018.
L'Oreal Invalidity Opinion Ex A43, filed Jul. 26, 2018.
L'Oreal Invalidity Opinion Ex A44, filed Jul. 26, 2018.
L'Oreal Invalidity Opinion Ex A45, filed Jul. 26, 2018.
L'Oreal Invalidity Opinion Ex A46, filed Jul. 26, 2018.
L'Oreal Invalidity Opinion Ex A47, filed Jul. 26, 2018.
Lab muffin "How Does Olaplex Hair Treatment Work?" http://www.labmuffin.com/2015/04/how-does-hair-treatment-work, 8 pages retrieved from the internet Jun. 24, 2016.
Law, Robert—Declaration dated Jul. 13, 2018, Filed by third party in GB 1605346.4 and GB 1813313.2.
Lewis excerpt from Hawley's Condensed Chemical Dictionary, 5 pages (1997).
*Liqwd* vs. *L'Oreal (UK) Ltd.*, Amended Invalidity Grounds Nov. 6, 2017.
Lipkowska, Zofia Urbalczyk, and Przemyslaw Gluzinski. "Molecular recognition of acyclic amines I: Co-crystallization of 2, 2'-(ethylenedioxy)-diethylamine with dicarboxylic acids." Supramolecular Chemistry 7.2: 113-118 (1996).

(56) References Cited

OTHER PUBLICATIONS

Majonis, et al., "Dual-purpose polymer labels for fluorescent and mass cytometric affinity bioassays," Biomacromolecules, 14(5):1503-13 (2013).
Mayo, et al., "Effect of Spacer Chemistry on the Formation and Properties of Linear Reversible Polymers", Journal of Polymer Chemistry, Part A: Polymer Chemistry, 51:5056-5066 (2013).
Memorandum filed in response to official action of Jun. 5, 2017 in corresponding Israel application No. 248989.
Memorandum in Response to Official Action of Oct. 7, 2018 in Israel application No. 248989 dated Jan. 24, 2019.
Memorandum Order in *Liqwd, Inc. et al.* v. *L'Oreal USA, Inc. et al.*, Case No. 1:17-cv-00014 (D. Del), denying Motion for Preliminary Injunction by Judge Sue L. Robinson (Jul. 6, 2017).
Mhaskar, et al., "Hair breakage index: An alternative tool for damage assessment of human hair", J. Cosmet. Sci., 62:203-207 (2011).
Mintel database entry for Bigen Permanent Powder Hair Colour (Jun. 2013).
Mintel database entry for Samy Fat Foam product (Oct. 2010).
Mintel Database Record ID 1999129, L'Oreal Preference Les Blondissimes Hair Colourant, 2013.
Mintel Database, Record ID 743114, Catzy Hair Colourant, 4 pages, Published Jul. 23, 2007.
Mintel Leave-in Hair and Scalp Nutrient, XP002743522, Database accession No. 10141004, Jun. 1, 2003.
Mintel Permanent Hair Colour, XP002743523, Database Accession No. 2061070, May 1, 2013.
Morgan, et al., "Interaction of Maleic Acid with Thiol Compounds", Biochemical Laboratory, Cambridge, 733-742 (1983).
MSDS Olaplex No. 1 Bond Multiplier, dated Jun. 2014.
MSDS Olaplex No. 2 Bond Perfector, updated Jul. 2014.
Murota, et al., "Emedastine Difumurate Inhibits Histamine-Induced Collagen Synthesis in Dermal Fibroblasts", J. Investig. Allergol. Clin. Immunol, 18(4):245-252, (2008).
Nair, et al., "The Thiol-Michael Addition Click Reaction: A Powerful and Widely Used Tool in Materials Chemistry", Chemistry of Materials, 26:724-744 (2014).
Nandagiri, Arun—Declaration signed Jan. 30, 2017 (Ex. 1008) with CV (Ex. 1016).
Nandagiri, Arun—Deposition transcript dated Mar. 2, 2018 (Ex 2055).
Nandagiri, Arun—Deposition transcript dated Mar. 14, 2018 (Ex 2057).
Nandagiri, Arun—Deposition transcript dated Oct. 6, 2017.
Nandagiri, Arun—Rebuttal Declaration dated Jan. 26, 2018 (Ex 1040).
Nandagiri, Arun—Rebuttal Declaration, pp. 1-7, Jan. 30, 2017.
Naver Encyclopedia, Trichology Dictionary: Developer, with English Translation (2003).
New Olaplex Usage Instructions label (Jun. 2014).
Notice of Intention to refuse Supplementary Examination Report SG (Singapore) Application No. 11201609005Q dated Jan. 7, 2021.
Notice of Opposition in EP (Europe) European Application No. EP 16720308.2 dated Jul. 14, 2020.
Notice of Opposition in EP (Europe) European Application No. EP 3142637 dated Jul. 29, 2020.
Notice of Re-Examaniation CN (China) Application No. 201580026038.9 dated Dec. 10, 2020 and English Summary Thereof.
Notice of Re-Examination CN (China) Application No. 201580026038.9 dated Jun. 10, 2021 and English Summary Thereof.
Notification of Grant for GB 1513932.2 mailed Oct. 4, 2016.
Office Action ARIPO AP/P/2015/008934, dated May 27, 2019.
Office Action AU (Australia) 2017251818, mailed May 31, 2019.
Office Action AU 2015258904 mailed Nov. 2, 2016 (Examination Report).
Office Action CA (Canada) 2,947,303 mailed Dec. 28, 2016.
Office Action CA (Canada) 2,947,303, mailed Mar. 19, 2019.
Office Action CA (Canada) 2,947,303, mailed May 12, 2017.
Office Action CA (Canada) 2947303—Sep. 17, 2018.
Office Action CA (Canada) 2947303, Mailed Oct. 10, 2018.
Office Action CA (Canada) CA 2,947,303 mailed Dec. 21, 2017.
Office Action CL (Chile) 201600158 mailed Jun. 18, 2018, with English Summary.
Office Action CL (Chile) 201602911—Sep. 27, 2018, with English Summary.
Office Action CL (Chile) 201602911 mailed Apr. 11, 2018, with English Translation.
Office Action CN (China) 201480042200.1 mailed Jan. 1, 2018.
Office Action CN (China) 201480042200.1 mailed May 2, 2017 (with English summary).
Office Action CN (China) 201480042200.1 with English summary, mailed Apr. 22, 2019.
Office Action CN (China) 201480042200.10 Dated Aug. 3, 2018 with English Summary.
Office Action CN (China) 201580026038.9—Sep. 5, 2018 with English Summary.
Office Action CN (China) 201580026038.9 with English summary, mailed Apr. 11, 2019.
Office Action CO (Colombia) 16-030.965 mailed Jul. 28, 2017 (with English summary).
Office Action CU (Cuba) 2016-0017 mailed Jan. 26, 2018 (English Translation).
Office Action CU (Cuban) 2016-0017 dated Jun. 20, 2018 (English Translation).
Office Action DO (Dominican Republic) P20160030 mailed Apr. 10, 2018 (English Summary).
Office Action DO (Dominican Republic) P20160030, mailed Sep. 18, 2018, with English Summary.
Office Action EA (Eurasia) 201592291 mailed May 8, 2018, with English Translation.
Office Action EA (Eurasia) 201592291, dated Aug. 30, 2018, with English Summary.
Office Action EA (Eurasia) 2016-92315 mailed Jan. 30, 2019 with English Summary.
Office Action EA (Eurasia) 201692315 mailed with English translation, Sep. 28, 2017.
Office Action EG (Egypt) 2016111820, dated Nov. 26, 2018, with English Translation.
Office Action EP (Europe) 15725209.9 dated May 16, 2019.
Office Action EP (Europe) 15725209.9 mailed Jan. 1, 2018.
Office Action EP (Europe) 15725209.9, mailed Aug. 15, 2018.
Office Action EP (Europe) 16798857.5 dated Feb. 19, 2019.
Office Action GB (United Kingdom) 1605344.9 mailed Apr. 29, 2016.
Office Action GE (Georgia) AP 2014 01404 mailed May 4, 2017 (with English translation).
Office Action HN (Honduras) 2016-000236 mailed Feb. 1, 2019 with English Translation.
Office Action IL (Israel) 248989 with Third Party Observation mailed Sep. 6, 2017 (English Summary).
Office Action IL (Israel) 248989, mailed Jun. 5, 2017 (with English summary).
Office Action IN (India) 20147007019.00, mailed Sep. 6, 2018, with English Translation.
Office Action IN (India) 201617038524, mailed May 12, 2018, with English Translation.
Office Action JP (Japan) 2016-572832 with English summary, mailed Dec. 11, 2018.
Office Action JP (Japan) 2016-572832, Aug. 2, 2018, with English Translation.
Office Action JP (Japan) 2016-572832, mailed Jul. 31, 2018, English Translation.
Office Action JP (Japan) 2017-152453 dated May 14, 2019, with English summary.
Office Action KR (Republic of Korea) 10-2016-7034158, mailed Apr. 10, 2017 (with English summary).
Office Action MX (Mexico) MX/a/2016/014917, mailed Jun. 20, 2018.
Office Action MX (Mexico) MXa/2016/00176 mailed Aug. 24, 2017.
Office Action NZ (New Zealand) 725652 mailed Apr. 3, 2017 (Examination Report).

(56) References Cited

OTHER PUBLICATIONS

Office Action SA (Saudi Arabia) 516370509, received Aug. 1, 2017 with English Summary.
Office Action SG (Singapore) 11201609005Q, dated May 24, 2017.
Office Action SG (Singapore) 11201609005Q, Dated Nov. 29, 2017.
Office Action SG (Singapore) 11201609005Q, dated Sep. 28, 2018.
Office Action SV (El Salvador) 20160019660, mailed Mar. 14, 2018, with brief English Summary.
Office Action SV (El Salvador) 2016005320, Mailed Oct. 5, 2018.
Office Action UA (Ukraine) a201601137 mailed Jun. 22, 2017 (with English translation).
Office Action UK (United Kingdom) 1618547.2 mailed Nov. 30, 2016.
Office Action U.S. Appl. No. 14/713,885, dated Aug. 17, 2015.
Office Action U.S. Appl. No. 15/087,415, dated May 23, 2016.
Office Action U.S. Appl. No. 15/290,593 mailed Jan. 2, 2018.
Office Action U.S. Appl. No. 15/290,593, dated Aug. 1, 2018.
Office Action U.S. Appl. No. 15/415,464 ,mailed Mar. 15, 2017.
Office Action U.S. Appl. No. 15/626,453 dated May 14, 2019.
Office Action U.S. Appl. No. 15/854,504, mailed Mar. 7, 2019.
Office Action U.S. Appl. No. 15/855,719, mailed Mar. 25, 2019.
Office Action U.S. Appl. No. 15/940,150, dated May 16, 2018.
Office Action U.S. Appl. No. 15/955,455, dated Jun. 26, 2018.
Office Action AU (Australia) 2015258904 mailed Oct. 26, 2017.
Office Action BR (Brazil) 1120160022556, dated Aug. 6, 2019, with English Summary.
Office Action BR (Brazil) 112016026378-2 dated Oct. 15, 2019, with English Summary.
Office Action BR (Brazil) 112016026378-2, dated Aug. 14, 2019, with English Summary.
Office Action CA (Canada) 2947303, dated Jul. 12, 2019.
Office Action CN (China) Application No. 201480042200.1 dated Dec. 9, 2020 with English Summary.
Office Action CN (China) 201480042200.10, Dated Nov. 9, 2018, with English Summary.
Office Action CN (China) 201580026038.90 mailed Dec. 18, 2017, with English Summary.
Office Action CN (China) 201580026039, dated Jul. 16, 2019 with English Summary.
Office Action CN (China) Application No. 201580026038.9 dated Nov. 25, 2020 with English Summary.
Office Action CN (China) Application No. 201680088959.2 with English Summary dated Dec. 3, 2021.
Office Action CR (Costa Rica) Application No. 20160053 dated Dec. 9, 2020 with English Summary.
Office Action CU (Cuba) 2016-0017 dated Jul. 3, 2018 (with English Translation).
Office Action EA (Eurasia) 201592291, dated Jul. 9, 2019, with English Translation.
Office Action EA (Eurasia) 201692315 mailed May 17, 2018, with English Translation.
Office Action EA (Eurasia) 201692315, with English Translation, dated Oct. 23, 2019.
Office Action EA (Eurasia)201592291 mailed Aug. 1, 2017.
Office Action EP (Europe) 17163334, dated Jun. 18, 2019.
Office Action EP (Europe) 17163334.0 mailed Apr. 26, 2018.
Office Action EP (Europe)15725209.9, mailed May 18, 2017.
Office Action for KR (Republic of Korea) 10-2016-7034158 mailed May 17, 2018 (with English Translation).
Office Action GB (United Kingdom) 1813313.2, mailed Sep. 20, 2018.
Office Action HN (Honduras) Application No. 2016-002313 dated Dec. 23, 2020 with English Summary.
Office Action ID (Indonesia) P00201600646, mailed Jan. 21, 2019 with English Translation.
Office Action ID (Indonesia) Application No. POD 201608726 with English Summary dated Nov. 17, 2021.
Office Action ID (Indonesia) P00201600646, dated May 25, 2018, with English Translation.
Office Action IL (Israel) 248989 (with third party submission) mailed Sep. 6, 2017 (English Summary).
Office Action IL (Israel) 248989 mailed Mar. 4, 2018 (English Summary).
Office Action IL (Israel) 248989 with brief English summary mailed Sep. 23, 2020.
Office Action IN (India) 201647007019, dated Aug. 2, 2019 with English Translation.
Office Action Japanese Appeal No. 2018-15999; JP (Japan) 2016-572832, dated Nov. 19, 2019 with English Translation.
Office Action JP (Japan) 2016-572832, dated Oct. 26, 2017 (English Translation).
Office Action JP (Japan) 2016-515948, mailed Jun. 27, 2017, English Tranlsation.
Office Action JP (Japan) 2016-515948, mailed Oct. 3, 2017.
Office Action JP (Japan) 2016-515948, mailed Jun. 27, 2017.
Office Action JP (Japan) 2016-572832 mailed Jun. 2, 2017 (with English summary).
Office Action JP (Japan) 2017-152453 with English summary, mailed Oct. 30, 2018.
Office Action JP (Japan) Japanese Application No. 2017-555304 dated Mar. 18, 2020 with English Summary.
Office Action JP (Japan) Japanese Office Action for Japanese Application No. 2017-555304 dated Nov. 30, 2020 with English Summary.
Office Action MX (Mexico) MX/a/2016/014917, dated Apr. 12, 2019 with English Summary.
Office Action MX (Mexico) MX/a/2016/014917, Dec. 7, 2018, with English Summary.
Office Action MY (Malaysia) PI 2016700195 dated Sep. 30, 2019.
Office Action NZ (New Zealand) 725652 mailed Oct. 13, 2017 (Examination Report).
Office Action NZ (New Zealand) 725652, mailed May 22, 2018 (Examination Report).
Office Action of IL (Israel) 248989, Mailed Oct. 7, 2018 with English Summary.
Office Action PA (Panama) 91008-01 mailed Jan. 31, 2017 (with English summary).
Office Action SA (Saudi Arabia) 516370509, mailed May 25, 2017 (with English summary) (Examination Report).
Office Action SV (El Salvador) Application No. 2016-0019660 dated Mar. 18, 2019 with English Summary.
Office Action SV (El Salvador) Application No. 2016-0020933 with English Summary dated Apr. 19, 2021.
Office Action U.S. Appl. No. 16/571,933 dated Apr. 9, 2021.
Office Action U.S. Appl. No. 15/854,504 dated Aug. 8, 2019.
Official communication in UK Patent Application 1513932.2 (Apr. 13, 2016).
Ogata and Sawaki, et al., "Kinetics of the Acid-Catalysed Formation of Aliphatic Peracids from Hydrogen Peroxide and Aliphatic Acids in Dioxin" Tetrahedron, 21:3381-3386, (1965).
Olaplex "The Olaplex Difference" https://olaplex.com/pages/how-it-works, retrieved from the internet Dec. 12, 2017.
Olaplex Bond Mulitplier No. 1 Mix with Highlights, balayage, or high lift color label (Jun. 2014).
Olaplex on Instagram page, https://www.instagram.com/p/mGhswioJQ2/?hl=en, Mar. 28, 2014.
Olaplex on Instagram page, https://www.instagram.com/p/mvxsbUoJSI/?hl=en, Apr. 13, 2014.
Olaplex on Instagram post, Feb. 22, 2015 http://www.instagram.com/p/zacpQulJfn/.
Olaplex on Instragram page, https://www.instagram.com/p/nBwLbtoJck/?hl=en, Apr. 20, 2014.
Olaplex, Apparent description of booth presentation during Bronner Bros. show in Atlanta http:// www.instagram.com/p/zacpQulJfn/, Instagram post Feb. 22, 2015.
Olaplex, Material Safety Data Sheet for Olaplex Bond Multiplier No. a Dec. 2014.
Olaplex.com, "Never break a client's hair", visited Jun. 28, 2014.
Partial International Search Report for PCT application, PCT/US2015/065032, mailed May 9, 2016.
Partial International Search Report for PCT/US2015/031166 mailed Sep. 14, 2015.

(56) References Cited

OTHER PUBLICATIONS

Paterson, et al., "On the synthesis of N-maleoyl amino acids in aqueous media: cautionary tales for the unwary traveller", Arkat USA, Inc., 11-16 (2010).
PGR 2017-00011 Decision denying Institution of Post-Grant Review, by Patent Trial and Appeal Board, Paper 24 (Jul. 19, 2017).
PGR 2017-00012 Petition for Post-Grant Review of U.S. Pat. No. 9,498,419, filed on behalf of L'Oreal USA, Inc. (Jan. 31, 2017).
PGR 2017-00012—Redacted version of Paper 102, Final Written Decision, Jun. 27, 2018 (Paper 105).
PGR 2017-00012 Decision partial Institution of Post-Grant Review, by Patent Trial and Appeal Board, Paper 17 (Jul. 19, 2017).
PGR 2017-00012 Liqwd, Inc.'s Patent Owner Response under 37 C.F.R. §42.220, filed on Oct. 20, 2017 (Redacted).
PGR 2017-00012 Patent Owner's Supplemental Response, May 24, 2018.
PGR 2017-00012 Petitioner's Reply to Patent Owner's Supplemental Response May 31, 2018.
PGR 2017-00012 Redacted Petitioners reply to patent owner's response, pp. 1-32 Jan. 26, 2018.
PGR 2018-00023—Wickett, Randall Declaration dated Jan. 31, 2018.
PGR 2018-00023 Paper 9 Institution Denied, Aug. 10, 2018.
PGR 2018-00023 Patent owner's preliminary response, pp. 1-76, May 21, 2018.
PGR 2018-00023 Redacted Petition for Post-Grant review of U.S. Pat. No. 9,668,954 dated Jan. 31, 2018.
PGR 2018-00024—Wickett, Randall Declaration dated Jan. 31, 2018.
PGR 2018-00024 Paper 12 Institution Denied, Aug. 10, 2018.
PGR 2018-00024 Patent owner's preliminary response, pp. 1-76, May 21, 2018.
PGR 2018-00024 Redacted Petition for Post-Grant review of U.S. Pat. No. 9,668,954 dated Jan. 31, 2018.
PGR 2018-00025—Wickett, Randall Declaration Feb. 15, 2019.
PGR 2018-00025 Paper 12 Institution Decision, Aug. 10, 2018.
PGR 2018-00025 Patent owner's preliminary response, pp. 1-51, May 21, 2018.
PGR 2018-00025 Petition for Post-Grant review of U.S. Pat. No. 9,668,954 (Redacted) dated Feb. 1, 2018.
PGR 2018-00025; EX 1062; Wickett Reply Declaration, Redacted, dated Feb. 15, 2019.
Plaintiff's Opening Brief in Support of Motion for Preliminary Injunction, redacted-public version, filed Jan. 18, 2017.
Po and Senozan article re: Henderson-Hasselbalch Equation, 2001 (Exhibit 2052).
Pomogailo, et al., "Monomeric and Polymeric Carboxylic Acids", Springer Series in Materials Science, 138(2):7-25 (2010).
Pramanik, "10.3.7 OS-Salt Interaction", Characterization of Impurities and Degradants Using Mass Spectrometry, John Wiley & Sons, Hoboken, New Jersey, (2011).
Pressly, Eric D.—Declaration, signed Oct. 19, 2017 (Redacted) filed in PGR 2017-00012.
Printout of the webpage http://www.olaplex.com/pages/patent, taken on Sep. 22, 2016.
Prior Use—documentary Evidence E36 as provided on parent case NZ725652 Evidence of public prior use before May 5, 2014.
Product Information for Maxton Bleach Powder (May 2006).
Public Version of Final Written Decision, dated Jul. 30, 2019.
Quantitative Chemical Analysis, pp. 1027-1 thru 1027-5, Daniel Harris Editor, 3rd Ed., (1991).
Ramachandra, et al., "Acid-based characteristics of human hair: Absorption of HCl and NaOH, and the effects on physical properties." J Soc Comet Chem., 32:393-405 (1981).
Randebrock, "Neue Erkenntnisse Uber den morphologischen aufbau des menschlichen haares," J Soc Cos. Chem., 15:691-706 (1964).
Redacted Version of Declaration of Robert J.W. Hefford, PhD with Appendices (1-3) and Exhibits (A-0), filed in *Liqwd, Inc. et al. v. L'Oreal USA, Inc. et al.*, U.S. District Court for the District of Delaware, Civil Action No. 1:17-cv-00014 on Apr. 17, 2017.

Refinery, "Fire Your Colorist if They Are Not Using This" http://www.refinery20.com/olaplex-hair-color, 6 pages, retrieved from the internet Jun. 24, 2016.
Relaxing agents, Milady Standard Cosmetology, pp. 618-625, 13th edition, (2016).
Robbins and Crawford, et al., "Cuticle Damage and the Tensile Properties of Human Hair", J. Soc. Cosmet. Chem. , 42:59-67 (1991).
Robbins, Chapter 10, "Definitions of Consumer Relevant Hair Assembly Properties and How These are Controlled by Single Fiber Properties", Chemical and Physical Behavior of Human Hair, 5th Edition, 2012.
Robbins, Chapter 4 "Bleaching Human Hair" in Chemical and Physical Behavior of Human Hair, 2002.
Robbins, Chapter 5 "Bleaching and Oxidation of Human Hair" in Chemical and Physical Behavior of Human Hair 2012.
Robbins, Chapter 6 "Interactions of Shampoo and Conditioner Ingredients with Hair" in Chemical and Physical Behavior of Human Hair 2012.
Robbins, Clarence R., Mouhatu no kagaku [Science of Hair], 4th edition, FragranceJournal Ltd.,Jul. 10, 2006, p. 221-225 with English counterpart, p. 194-198.
Robbins, et al., "Chemical Composition of Different Hair Types" Chemical and Physical Behavior of Human Hair ,Chapter 2:104-76, Springer-Verlag, Berlin Heidelberg (2012).
Robbins, et al., "Dyeing Human Hair", Chemical and Physical Behavior of Human Hair, Chapter 7, Springer-Verlag, Berlin Heidelberg (2012).
Robbins, et al., "Polymerization into Human Hair", J. Soc. Cosmet. Chem., 25:407-421 (1974).
Robbins, et al., "The Physical Properties of Hair Fibers", Chemical and Physical Behavior of Human Hair, Chapter 9, Springer-Verlag, Berlin Heidelberg (2012).
Robinson, "A study of damaged hair", J. Soc. Cosmet. Chem., 27:155-161 (1976).
Ruetsch, et al., "Photodegradation of human air: An SEM study", J. Cosmet. Sci., 51:103-125 (2000).
Sandhu, et al., "A simple and sensitive method using protein loss measurements to evaluate damage to human hair during combing", J. Soc. Cosmet. Chem., 46:39-52 (1995).
Second Written Opinion for corresponding Singapore Application No. 11201609005Q mailed Nov. 29, 2017.
Shansky, "Toning of Human Hair with Fiber Reactive Dyestuffs," Cosmetics and Toiletries, 91(11):46-48 (1976).
Shansky, "The Reaction Mechanism of Fiber Reactive Dye stuffs with Hair Keratin," American Perfumer and Cosmetics (1966).
Sigma-Aldrich website BM PEG 3 1 11 Bismaleimido Triethyleneglycol (2018).
Slavin, et al. "Biological surface modification by 'thiol-ene' addition of polymers synthesized by catalytic chain transfer polymerization (CCTP)," Polymer Chem., 3:1461-6 (2012).
Statement—Amended Reply Statement of Case on Validity (KR970, WO768 and Catzy), dated Nov. 28, 2017.
Statement—Reply Statement of Case on Validity (Olaplex), dated Nov. 28, 2017.
Statement of Case on the Term "Simple Salt", dated Jan. 10, 2018.
Statement of Case on Validity (KR970, WO768 and Catzy), dated Nov. 6, 2017.
Statement of Grounds and Particulars in Opposition Proceeding in AU (Australia) Application No. 2017251818 filed May 1, 2020.
Success Stories presentation, Oct. 6, 2016.
Swift, Chapter 10, "Mechanical Properties of Hair" in Fundamentals of Human Hair Science, (1997).
Swift, Chapter 11, "Cosmetic Treatments of Hair" in Fundamentals of Human Hair Science, (1997).
Swift, Fundamentals of Human Hair Science, (1997).
Table 2 from Furia, T.E., Sequestrants in Food (Chp. 6) in CRC Handbook of Food Additives (1972).
Table 3.4, pKa values of some amino acids, From: Appendix: Acid-Base Concepts Biochemistry 5th edition. Berg JM, Tymoczko JL, Stryer L.New York: W H Freeman; (2002).
Tate, et al., "Quantification and prevention of hair damage", J. Soc. Cosmet. Chem., 44:347-371 (1993).

(56) References Cited

OTHER PUBLICATIONS

The Power Of One http://www.nxtbook.com/nctbooks/creativeage/Launchpad_201405/index.php?srartid, 401 page, retrieved from the internet Jun. 24, 2016.
Thermo Fisher Scientific ,"Bismaleimide Cross linkers (BMOE, BMBandBMH)," product instructions, pp. 1-3 (2012).
Thermo Scientific, "Instructions BM (PEG) 2 and BM (PEG) 3" (2012).
Third party observation for GB 1513932.2 (Jan. 2016).
Third Party Observation AU (Australia) 2017251818, dated Jun. 17, 2019.
Third Party Observation for JP (Japan) 2016-572832 with English Translation dated Apr. 19, 2019.
Third Party Observation AU (Australia) 2015258904 mailed Dec. 19, 2016.
Third Party Observation AU (Australia) 2017251818, dated Oct. 2, 2019.
Third Party Observation AU (Australia) 2017251818, filed Jun. 4, 2019.
Third Party Observation BR (Brazil) 1120160263782 Jan. 9, 2018 w/Eng Summary.
Third Party Observation BR (Brazil) 1120160263782 Oct. 23, 2018 w/Eng Summary.
Third Party Observation CA (Canada) 2947303 filed Feb. 19, 2019.
Third Party Observation CA (Canada) 2947303, dated Jan. 14, 2020.
Third Party Observation CA (Canada) 2947303, dated Oct. 25, 2019.
Third Party Observation CA (Canada) 2947303, filed Jun. 12, 2019.
Third Party Observation EA (Eurasia) 201692315, dated Sep. 13, 2019 , with English Translation.
Third Party Observation EP (Europe) 15725209.9 filed Feb. 22, 2019 with Eng Translation.
Third Party Observation EP (Europe) 15725209.9 filed Nov. 15, 2019.
Third Party Observation EP (Europe) 15725209.9, dated Nov. 29, 2019.
Third Party Observation filed EP (Europe) 14758005.4 (May 13, 2016).
Third Party Observation filed EP14758005.4 (May 18, 2016).
Third Party Observation filed GB1513932.2 (Oct. 3, 2016).
Third Party Observation filed GB1513932.2 (Aug. 23, 2016).
Third Party Observation filed GB1513932.2 (Sep. 22, 2016).
Third Party Observation filed GB1605346.4 (Nov. 11, 2016).
Third Party Observation filed in AU (Australia) 2017251818, mailed Jan. 17, 2018.
Third Party Observation filed in AU (Australia) Application No. 2015258904 mailed Oct. 5, 2017.
Third Party Observation filed in EP (Europe) Application No. 15725209.9 mailed Oct. 27, 2017.
Third Party Observation filed in GB Application No. 1513932.2 (Jan. 2016).
Third Party Observation filed in ID (Indonesia) Application No. 2017/09919 dated May 19, 2020.
Third Party Observation filed in IL (Israel) Application No. 265590 dated Mar. 26, 2020.
Third Party Observation filed in JP (Japan) Application No. 2016-572832, mailed May 25, 2018, with English Summary).
Third Party Observation filed in JP Application No. 2016-572832 mailed Sep. 29, 2017.
Third Party Observation filed in KR (Korea) 101787310 on Jan. 29, 2019 (English Translation).
Third Party Observation filed in MX (Mexico) Application No. MX/a/2016/014917 mailed Nov. 6, 2017.
Third Party Observation filed in NZ (New Zealand) Application No. 725652, mailed May 16, 2018—Part 2 of 2.
Third Party Observation filed in NZ (New Zealand) Application No. 725652, dated Mar. 5, 2021.
Third Party Observation filed in NZ (New Zealand) Application No. 725652, mailed May 16, 2018—Part 1 of 2.
Third Party Observation filed in SG (Singapore) Application No. 11201609005Q dated Apr. 5, 2019.
Third Party Observation filed in SG (Singapore) Application No. 11201609005Q dated Dec. 27, 2018.
Third Party Observation filed in SG (Singapore) Application No. 11201609005Q dated Dec. 8, 2017.
Third Party Observation filed in SG (Singapore) Application No. 11201609005Q dated Feb. 15, 2018.
Third Party Observation filed in SG (Singapore) Application No. 11201609005Q dated May 25, 2018.
Third Party Observation filed in U.S. Appl. No. 15/087,415, Aug. 29, 2016.
Third Party Observation filed in U.S. Appl. No. 15/087,415, Sep. 14, 2016.
Third Party Observation filed in U.S. Appl. No. 15/087,415, Aug. 25, 2016.
Third Party Observation filed in U.S. Appl. No. 15/087,415, Sep. 23, 2016.
Third Party Observation for EA (Eurasia) 201692315, filed Nov. 1, 2017, (English Translation).
Third Party Observation for EC (Ecuador) IEPI 2016-94261, filed Mar. 29, 2017, with English Summary.
Third Party Observation for EP (Europe) 15725209.9 filed May 8, 2019.
Third Party Observation for GB 1605346.4 , dated Oct. 24, 2018.
Third Party Observation for GB 1605346.4, filed Nov. 30, 2018.
Third Party Observation for GB 1813313.2, dated Jan. 8, 2019.
Third Party Observation for IL (Israel) 248989, mailed Oct. 3, 2018 (English Translation).
Third Party Observation GB 1813313.2 filed Apr. 2, 2019.
Third Party Observation GB 1813313.2 filed Mar. 8, 2019.
Third Party Observation GB1513932.2 (Jun. 24, 2016).
Third Party Observation ID (Indonesia) Application No. P00201608726, with English Translation, mailed Mar. 6, 2018.
Third Party Observation IL (Israel) 248989 mailed Jan. 10, 2018 (English Translation).
Third Party Observation IN (India) 2016177038524 on Feb. 6, 2019 (English Translation).
Third Party Observation JP (Japan) 2016-572832 filed Sep. 2, 2019 with English summary.
Third Party Observation JP (Japan) 2016572832 filed Mar. 5, 2019 with Eng Summary.
Third Party Observation KR (Korea) 101787310 on Jan. 29, 2019.
Third Party Observation mailed EP (Europe) 157250209.9 (Jan. 10, 2017).
Third Party Observation mailed EP (Europe)14758005.4 (Dec. 21, 2016).
Third Party Observation New Zealand NZ (New Zealand) 725652 mailed Dec. 19, 2016.
Third Party Observation Submitted GB 1513932.2 (Apr. 20, 2016).
Third Party Observation, EP (Europe) 15725209.9, mailed Aug. 22, 2018.
Third Party Protest filed in CA (Canada) 2,947,303, mailed Dec. 7, 2017.
Third Party Protest filed in CA (Canada) 2,947,303, mailed May 8, 2018.
Third Party Protest for CA (Canada) 2947303, mailed Feb. 8, 2017.
Third Party Submission for CA (Canada) 2,947,303, dated Sep. 14, 2018.
Thomas Clausen et al., Hair Preparations, in Ullman's Encyclopedia of Industrial Chemistry (Jul. 15, 2006).
Tracey Cunningham on Instagram page; https://www.instagram.com/p/l_mat6ig-z/, (Mar. 26, 2014).
Tracey Cunningham on Instagram page; https://www.instagram.com/p/11AF_Zig5e/, (Mar. 22, 2014).
UK High Court Judgement—Jun. 11, 2018—In Relationship to GB 2525793.
Voet, et al., Fundamentals of Biochemistry Excerpt (2008).
Webster's Third International New Dictionary 40 (3rd ed) 2002.
Wenniger, et al., "Maleic Acid", CTFA Cosmetic Ingredient Handbook, 2:226 (1992).
Whewell, "The chemistry of hair" pp. 207-223 A lecture delivered before the Society Dec. 14, 1960.

(56) References Cited

OTHER PUBLICATIONS

White and Emmons, et al., "The Chemistry of Permaleic Acid", Tetrahedron, 17:31-34, (1962).
Wicket and Jachowicz, "Measuring Hair", Handbook of Cosmetic Science and Technology pp. 694-724 Andre Barrel #rd. Ed, (2009).
WPI Accession No. 1995-355152, English abstract of JPH 07242520, Sep. 19, 1995 (retrieved Feb. 2, 2016).
Written Opinion for PCT/US2015/031166, mailed Jul. 19, 2016.
Written Opinion for SG (Singapore) Application No. 11201609005Q dated May 7, 2020.
Yan, et al., "Cellular association and cargo release of redox-responsive polymer capsules mediated by exofacial thiols," Adv. Mater. 23:3916-3921 (2011).
Yang, et al., "In-Situ Polymerization of Maleic Acid and Itaconic Acid and Crosslinking of Cotton Fabric", Textile Res. J., 69(10):782-789 (1999).
Yang, et al., "Polymerization of Maleic Acid and Itaconic Acid Studied by FT-Raman Spectroscopy", J. Applied Polymer Science, 81:223-228 (2001).
Zhao, et al., "Preparation of peracetic acid from hydrogen peroxide Part I: Kinetics for peracetic acid synthesis and hydrolysis" Journal of Molecular Catalysis A: Chemical, 271:246-252 (2007).
Zumdahl, Chemistry Excerpt, 15:621-622 (1986).
Zviak "The Science of Hair Care," Marcel Dekker, Inc., pp. 263-279 (1986).
Zviak & Millequant Chapter 7, "Hair Bleaching" in The Science of Hair Care, (2005) (Exhibit DH 3).
Zviak & Millequant Chapter 9 "Oxidation Colouring", The Science of Hair Care, Informa Healthcare USA, Inc (2008).
Zviak, et al., "Hair Structure, Function, and Physicochemical Properties", The Science of Hair Care, Chapter 1, 1-48 (1986).

* cited by examiner

METHODS FOR FIXING HAIR AND SKIN

CROSS-REFERENCE TO RELATED APPLICATIONS

The present application is a continuation of U.S. application Ser. No. 18/177,011 filed Mar. 1, 2023, which is a continuation of U.S. application Ser. No. 17/941,675 filed Sep. 9, 2022, which is a continuation of U.S. application Ser. No. 16/830,789 filed Mar. 26, 2020 (now U.S. Pat. No. 11,446,525), which is a continuation of U.S. application Ser. No. 15/854,504 filed Dec. 26, 2017 (now U.S. Pat. No. 10,639,505), which is a continuation of U.S. application Ser. No. 14/835,223 filed Aug. 25, 2015 (now U.S. Pat. No. 9,855,447), which is a continuation of U.S. application Ser. No. 14/748,831 filed Jun. 24, 2015 (now U.S. Pat. No. 9,144,537), which is a continuation of U.S. application Ser. No. 14/459,012 filed Aug. 13, 2014 (now U.S. Pat. No. 9,095,518), which is a continuation-in-part of International Application PCT/US2014/049388 filed Aug. 1, 2014, which claims priority to U.S. Prov. Application 61/861,281 filed Aug. 1, 2013; U.S. Prov. Application 61/867,872 filed Aug. 20, 2013; U.S. Prov. Application 61/885,898 filed on Oct. 2, 2013; U.S. Prov. Application 61/903,239 filed Nov. 12, 2013; U.S. application Ser. No. 14/257,089 filed Apr. 21, 2014; U.S. application Ser. No. 14/257,056 filed Apr. 21, 2014; U.S. application Ser. No. 14/257,076 filed Apr. 21, 2014; and U.S. Prov. Application 62/000,340 filed May 19, 2014. The contents of the referenced patent applications are incorporated into the present application by reference.

FIELD OF THE INVENTION

The present invention generally relates to compositions and methods for treating hair or skin, particularly for repairing disulfide bonds in hair or on the skin.

BACKGROUND OF THE INVENTION

Hair consists of many long protein chains composed of amino acid building blocks. These chains, or polymers, are bound to each other via 1) hydrogen bonding, 2) salt bridges between acid and base groups, and 3) disulfide bonds. Water reversibly cleaves the hydrogen bonds. This makes wet hair easy to shape and set. When the water evaporates, hydrogen bonds form at new positions, holding the hair in this set. In strongly acidic solutions, such as where the pH is 1.0 to 2.0, both hydrogen bonds and salt bridges are broken. The disulfide bonds, however, can still hold the protein chains together in the strand of hair under such conditions.

At a slightly alkaline pH of 8.5, some disulfide bonds are broken (Dombrink et al., Chem Matters, 1983, page 8). Repeated washing with slightly alkaline shampoo damages the hair by breaking more and more of the disulfide bonds. This causes the cuticle or outer surface of the hair strands to become ruffled and generally leaves the hair in a wet, tangled, and generally unmanageable state. This is one cause of "split ends." Once the hair dries, it is often left in a dry, rough, or frizzy condition. Additionally, rough hair catches light unevenly and makes the hair look lusterless and dull. The hair can also be left with increased levels of static upon drying, which can interfere with combing and result in a condition commonly referred to as "fly-away hair."

Disulfide linkages are also ruptured due to heating or use of various reducing treatments. Current compositions and methods for waving and straightening mammalian hair use reducing agents such as thioglycolic acid, particularly as the ammonium salt, to cleave the hair's cystine disulfide bonds. Once the disulfide bonds are broken, and the hair is placed in stress to establish the final style (e.g., straight, wavy, or curly) the disulfide bonds are reestablished. Oxidation to restore the reduced bonds can be achieved by simply exposing the hair to atmospheric oxygen, but this oxidation step is very slow and is of very little practical use. Generally, hydrogen peroxide or sodium bromate is used as the oxidizing agent. However, the newly formed disulfide bonds are under stress to maintain the hair's new shape, thus, they break easily resulting in a reversion of the hair style over time. In addition, the use of peroxides in the hair styling process can result in damaged hair, removal of non-natural color from the hair, and/or leave the hair frizzy. Furthermore, some latent free thiols may remain in the hair even after oxidative treatment.

Treatment with peroxides used in the hair styling process results in the following reaction:

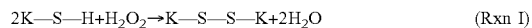

$$2K\text{—}S\text{—}H + H_2O_2 \rightarrow K\text{—}S\text{—}S\text{—}K + 2H_2O \quad \text{(Rxn I)}$$

where K represents keratin in the hair. However, if two K—S—H groups are not present for the reaction (Rxn I) to take place, it is believed that the following reaction takes place, which results in damaged hair.

$$K\text{—}S\text{—}H + 3H_2O_2 \rightarrow K\text{—}SO_2\text{—}OH + 3H_2O \quad \text{(Rxn II)}$$

Keratin is also a major component in skin. Damage to the disulfide bridges of keratin can cause skin to look unhealthy or flaky. Maintaining the disulfide bridges of keratin keeps the skin healthy and prevents cracking and splitting.

A variety of approaches have been developed to alleviate these problems, including post-shampoo application of hair conditioners, such as leave-on and rinse-off products. Typically, conditioning rinses put back the oily coating, especially to the damaged portion of the hair where the cuticle has become ruffled since conditioners cling best to these portions. However, too much or too heavy a conditioner will make the hair stickier, thus attracting dirt and often may make more shampooing treatments necessary. Typically conditioners do not bind the free thiols in hair.

The use of cationic polymers to form coacervates to provide conditioning benefits to the hair is known, such as described in International Published Applications WO 93/08787 to King et al. and WO 95/01152 to Napolione et al. Commonly used cationic deposition polymers include natural polymers, such as guar gum polymers, that have been modified with cationic substituents. The selection of a cationic guar polymer with sufficient charge density and molecular weight results in sufficient deposition of conditioning agents when incorporated in a shampoo or body wash. However, a relatively high level of such cationic guar polymer generally must be deposited on the hair or skin. Moreover, the cost of such cationic guar polymer is relatively high. As a result, incorporation of cationic guar polymer can increase the manufacturing costs of such shampoo compositions. Additionally, these shampoo compositions typically are useful for wet hair conditioning, but are not capable of delivering satisfactory dry hair smooth feel. Furthermore, these conditioners do not bind the free thiols in hair.

U.S. Pat. No. 5,656,265 to Bailey et al., discloses a hair styling conditioning process for use after treating the hair with a reducing agent. The process involves contacting the hair with a compound having an electrophilic group and at least one hydrophobic group. According to Bailey, the electrophilic groups react with the thiol groups to provide a plurality of hydrophobic groups on the hair. However, these conditioners do not bind the free thiols in hair together.

There is a need for hair formulations and treatments that can provide improved conditioning benefit for hair. Specifically, there is a need to provide long lasting moisturized feel, smooth feel, and manageability control to hair when it is dried. There is also a need for hair formulations and treatments that repair latent free thiols in the hair.

There is a need for hair formulations and treatments that repair and/or strengthen damaged hair and rebuild stronger bonds in hair treated with reducing agents.

There is also a need for skin formulations and treatments that provide improved conditioning and/or moisturizing benefit to the skin. In particular, there is a need to provide a long lasting moisturized and smooth feel to the skin. There is also a need for skin formulations and treatments that repair free thiols in the skin.

Therefore, it is an object of this invention to provide improved compositions and methods for repairing and/or strengthening damaged hair.

It is also an object of this invention to provide compositions and methods for using these compositions that repair and/or strengthen hair after a washing or reducing treatment.

It is also an object of this invention to provide compositions and methods for conditioning, moisturizing, and/or otherwise treating the skin.

SUMMARY OF THE INVENTION

Compositions, kits, and methods for repairing bonds, for example, disulfide bonds, in hair or on the skin that have been damaged are disclosed. The compositions provide improved conditioning benefit for dry hair or moisturize the skin. Specifically, the compositions provide long lasting moisturized feel and smooth feel without leaving the hair greasy, improved appearance (e.g., sheen), increased dry strength (tensile strength), ease of combing the hair when wet or dried, less hair breakage, and decreased frizz. The compositions also provide a long lasting moisturized feel and smooth feel to the skin.

The compositions contain one or more compounds that interact with keratin through more than one binding events (e.g., absorption, binding, etc.) which may involve reaction with one or more thiols in the hair or on the skin. Binding herein is defined as the formation of covalent, ionic or hydrogen bonding, etc. Under normal hair washing conditions, including shampooing and conditioning, the covalent bonds formed are not susceptible to reduction or hydrolysis. Use of the binding compositions prevents reversion of the hair's repaired bonds to their free thiol state, for at least one week, two weeks, three weeks, four weeks, one month, or two months, or longer, after application of the composition.

Improved methods of styling hair, for example permanent hair waving, hair curling, and hair straightening are also provided. The binding compositions can be applied each time the hair is washed or daily, once-weekly, twice-weekly, biweekly, once-monthly, every other month, or at less frequent intervals. Preferably, the binding compositions are applied weekly or once per month to achieve the desired results.

Traditional methods of permanent hair waving, hair curling, or straightening use hydrogen peroxide to rebuild the disulfide bonds after a reducing treatment. The process generally takes about three days to complete. The methods disclosed herein use binding agents to repair the hair; these binding agents are washed from the individual's hair on the same day that they are applied to the hair. In some embodiments, the binding agents and the free thiol groups form a carbon-sulfur covalent bond. Under the same conditions, such as temperature and moisture, hair treated with the binding agents takes a longer time to revert to its prior state compared to the same hair that is untreated. The binding agent can contain one or more reactive groups where the reactive functional groups are bound to the surface.

In one embodiment, the binding agent contains a linker or spacer and two or more reactive functional groups, wherein the reactive functional groups are covalently bound to the linker or spacer. In other embodiments, the binding agent contains a spacer or linker which forms a salt with the two or more reactive functional groups. In other embodiments, the binding agent contains one or more reactive groups where the reactive functional groups interact with the surface of the hair or functional groups on the hair.

DETAILED DESCRIPTION OF THE INVENTION

I. Definitions

The term "hair" refers to one or more than one strand of hair, as well as the natural components of hair, such as oil from a body. Hair also refers to virgin hair or processed hair, for example hair that has been exposed to hair waving or hair straightening formulations.

An "effective amount," e.g., of the binding agent or compositions described herein, refers to an amount of the binding agent in a composition or formulation which, when applied as part of a desired dosage regimen, binds free thiols in the hair.

"Pharmaceutically acceptable" and "cosmetically acceptable" are used interchangeably and refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. More specifically, pharmaceutically acceptable refers to a material, compound, or composition which is suitable for use in contact with the skin, scalp, or hair. Pharmaceutically acceptable materials are known to those of ordinary skill in the art.

"Shampoo," as used herein, generally refers to a liquid or semi-solid formulation applied to the hair that contains detergent or soap for washing the hair.

"Conditioner," as used herein, generally refers to a formulation (e.g., liquid, cream, lotion, gel, semi-solid) applied to the hair to soften the hair, smooth the hair, and/or change the sheen of the hair.

"Analog" and "Derivative" are used herein interchangeably and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Electrophilic group" or "electrophilic moiety" are used interchangeably and refer to one or more functional groups or moieties that have an affinity for or attract electrons.

"Michael acceptor," as used herein, is a species of electrophilic groups or moieties that participates in nucleophilic addition reactions. The Michael acceptor can be or can contain an α,β-unsaturated carbonyl-containing group or moiety, such as a ketone. Other Michael acceptors include pi-bonds, such as double or triple bonds conjugated to other pi-bond containing electron withdrawing groups, such as nitro groups, nitrile groups, and carboxylic acid groups.

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl," as used herein, refer to unsaturated aliphatic groups containing one or more double or triple bonds analogous in length (e.g., C2-C30) and possible substitution to the alkyl groups described above.

"Aryl," as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar," as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl," "aryl heterocycles," or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, perfluoroalkyl, and cyano. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl," as used herein, refers to an alkyl group substituted with an aryl group (e.g., an aromatic or hetero aromatic group).

"Heterocycle" or "heterocyclic," as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, (C1-4) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl," as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, (C1-C8) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benzyl-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl (or its N-oxide), thienyl, pyrimidinyl (or its N-oxide), indolyl, isoquinolyl (or its N-oxide), quinolyl (or its N-oxide), and the like.

"Halogen," as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted C3-C20 cyclic, heterocyclic, substituted heterocyclic, amino acid, peptide, and polypeptide groups.

Heteroatoms, such as nitrogen, may have hydrogen substituents and/or any permissible substituents of organic compounds described herein that satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Polymer," as used herein, refers to a molecule containing more than 10 monomer units.

"Water-soluble," as used herein, generally means at least 10, 50, 100, 125, 150, 200, 225, or 250 g is soluble in 1 L of water at 25° C.

"Binding agent," as used herein, refers to a molecule that forms covalent, ionic or hydrogen bonding, etc. with the hair and generally includes the formation of at least one covalent bond with a free thiol.

II. Binding Formulations

The formulations disclosed herein are concerned with treating hair or skin. In particular, the formulations can rebuild latent disulfide bonds in hair or skin. Additionally, the formulations may also react with free amines in the hair to provide a conditioning effect.

The formulations contain one or more binding agents (also referred to herein as "compounds" or "active agents").

The binding agents can be combined with one or more pharmaceutically acceptable carriers and/or excipients that are considered safe and effective to human hair, skin, and/or human scalp, and may be administered to an individual's hair without causing undesirable side effects, such as burning, itching, and/or redness, or similar adverse reactions. The formulations may further contain an excipient that renders the formulations neutral pH, or a pH ranging from about pH 3 to about pH 12, preferably from pH 5 to pH 8.

The binding agent is typically present in an amount ranging from about 0.01 wt % to about 50 wt % of the formulation, preferably from about from about 1 wt % to about 25 wt % of the formulation, more preferably from about 1 wt % to about 15 wt %, most preferably from about 1 wt % to about 10 wt %. Typically, the binding agent is about 2.5-3 wt % of the formulation.

The binding agent is stable in aqueous solution for a period of at least 2, 3, 4, 5, 6, 8, 9, 10, 11, or 12 months or longer at pH of 6 to 8 and a temperature of about 25-30° C., preferably about 25° C. "Stable" as used herein with respect to shelf-life means that at least 40, 45, 50, 55, 60, 65, 70, 75, 80, 85, 90, or 95% of the reactive moieties are intact or to the extent that the reactive moieties react with water, the resulting product is also electrophilic.

a. Binding Agent

The binding agent contains at least two reactive moieties capable of reacting with a thiol. The binding agent optionally contains a linker between the two or more reactive moieties. The linker forms two or more ionic bonds with the reactive moieties. The reactive moieties, upon reaction with thiol groups on the hair follicle, form bonds that are stable, for example, hydrolytically stable. "Stable," as used in reference to the bonds formed between thiol groups on hair follicles means the bonds remain intact for at least one week, two weeks, three weeks, four weeks, one month, or two months or longer when exposed to water at pH 6-8 at a temperature from about 5° C. to about 100° C., preferably from about 20° C. to about 75° C., more preferably from about 20° C. to about 50° C., more preferably from about 25° C. to about 40° C., most preferably from about 25° C. to about 30° C. In some embodiments, the temperature is about 25° C. It is also preferred that the binding reaction occurs around room temperature, for example, from about 15° C. to about 35° C., preferably from about 20° C. to about 30° C., more preferably from about 22° C. to about 27° C.

The binding agents typically have a low molecular weight and are compatible with aqueous or solvent delivery systems. In some embodiments, the compound is water-soluble. The low molecular weight is preferred, as it allows the molecule to diffuse in and out of hair at a reasonable rate. Molecular weights of less than 10,000 Da, 8,000 Da, 6,000 Da, 5,000 Da, 4,000 Da, 3,000 Da, 2,000 Da, or 1,000 Da are preferred. In some embodiments, the molecular weight is less than 1500 Da, preferably less than 800 Da, most preferably less than 500 Daltons to achieve sufficient diffusion rates in conventional aqueous hair care systems.

i. Binding Agents Defined by Formula I

In some embodiments, the binding agents have a structure according to Formula I:

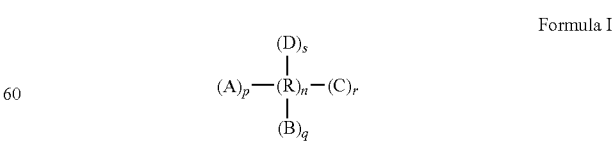

Formula I wherein A, B, C, and D are reactive moieties containing one or more charges, R is a linker that contains two or more charges, wherein the charges are opposite to the charges on the reactive moieties, and each occurrence of p, q, r, and s is independently an integer from 0 to 25, preferably from 0 to 10, more preferably from 0 to 2.

The sum of p+q+r+s is equal to or greater than 2.

The reactive moieties may be present on any atom of the linker. In some embodiments, the reactive moieties are the same. In some embodiments, one or more of the reactive moieties is different.

In some embodiments, the reactive moieties are negatively charged and the linker or spacer has positively charged moieties. In other embodiments, the reactive moieties are positively charged and the linker or spacer has negatively charged moieties. Generally, the sum of the charges on the binding agent of Formula I is zero though stoichiometric imbalances may exist.

ii. Linker

The reactive moieties on the binding agents are preferably linked via a linker. The term "linker," as used herein, refers to one or more polyfunctional, e.g. bifunctional molecules, trifunctional molecules, tetrafunctional molecules, etc., which can be used to ionically bound the two or more reactive moieties and which do not interfere with the reactive properties of the binding agents. The reactive moieties may be attached to any part of the linker.

Linkers can be a single atom, such as a heteroatom (e.g., O or S), a group of atoms, such as a functional group (e.g., amine, —C(=O)—, —CH2—), or multiple groups of atoms, such as an alkylene chain. Suitable linkers include but are not limited to oxygen, sulfur, carbon, boron, nitrogen, alkoxy, alkyl, alkenyl, cycloalkyl, cycloalkenyl, aryl, heterocycloalkyl, heteroaryl, ether, amine, and a polymer.

The linker is optionally independently substituted with one or more substituents including hydrogen, halogen, cyano, alkoxy, alkyl, alkenyl, cycloalkyl, cycloalkenyl, aryl, heterocycloalkyl, heteroaryl, amine, hydroxy, formyl, acyl, carboxylic acid (—COOH), —C(O)$R^1$, —C(O)O$R^1$, carboxylate (—COO$^-$), primary amide (e.g., —CONH$_2$), secondary amide (e.g., —CONH$R^1$), —C(O)N$R^1R^2$, —N$R^1R^2$, —N$R^1$S(O)$_2R^2$, —N$R^1$C(O)$R^2$, —S(O)$_2R^2$, —S$R^1$, and —S(O)$_2$N$R^1R^2$, sulfinyl group (e.g., —SO$R^1$), and sulfonyl group (e.g., —SOO$R^1$); wherein $R^1$ and $R^2$ may each independently be hydrogen, alkyl, alkenyl, alkynyl, cycloalkyl, aryl, heterocycloalkyl and heteroaryl; wherein each of $R^1$ and $R^2$ is optionally independently substituted with one or more substituents selected from the group consisting of halogen, hydroxyl, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or =O or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In some embodiments, the linker may be an alkoxy, ether, alkyl, alkenyl, cycloalkyl, cycloalkenyl, aryl, heterocycloalkyl, heteroaryl, amine, or a polymer. In some embodiments, the linker is not a polymer.

iii. Polymeric Binding Agents

The binding agent can be a polymer. In this form, the linker forms or is the polymer backbone having ionically associated therewith two or more reactive moieties. Optionally, the polymeric binding agent can have a structure according to Formula I. In some forms, for each occurrence of a monomer unit in the polymer, zero, one, two, three, four, or more reactive moieties can be ionically associated with, the monomer. The reactive moieties on each monomer unit in the polymer can be the same or different.

In some embodiments, at least one reactive moiety is present on each monomer unit. Alternately, the reactive moieties may be present on alternate monomer units. In some embodiments, reactive moieties are present on a minimum percentage of the monomer units in the polymer. For example, at least one reactive moiety can be present on 0.1%, 1%, 5%, 10%, 15%, 20%, 25%, 30%, 35%, 40%, 45%, 50%, 55%, 60%, 65%, 70%, 75%, 80%, 85%, 90%, 95%, or 100% of the monomer units in the polymer. The reactive moieties can be present on any atom on the monomer.

1. Polymers

The polymer may be functionalized at the termini (and/or within the polymer backbone) with one or more of reactive moieties, A-D. One or more monomers in the polymer may be functionalized so that one or more reactive moieties, A-D, may be introduced (e.g., ionically associated with) using techniques known in the art. For ionically associated moieties, the salt is typically generated in situ.

A wide variety of polymers and methods for forming the polymers are known in the art of polymer science. Polymers can be degradable or non-degradable polymers. Polymers can be natural or unnatural (synthetic) polymers. Polymers can be homopolymers or copolymers comprising two or more monomers. In terms of sequence, copolymers can be random, block, or comprise a combination of random and block sequences. The polymers can in some embodiments be linear polymers, branched polymers, or hyperbranched/dendritic polymers. The polymers may also be present as a bound particle or surface functionalized inorganic particle. Suitable polymers include, but are not limited to poly (vinyl acetate), copolymers of styrene and alkyl acrylates, and copolymers of vinyl acetate and acrylic acid, polyvinylpyrrolidone, dextran, carboxymethylcellulose, polyethylene glycol, polyalkylene, polyacrylates, and polymethacrylates; polyanhydrides; polyorthoesters; polystyrene (PS), poly (ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly (butadiene maleic anhydride-co-L-dopamine) (pBMAD), poly(butadiene maleic anhydride-co-phenylalanine), poly (butadiene maleic anhydride-co-tyrosine), poly(bis carboxy phenoxy propane-co-sebacic anhydride) (poly (CCP:SA)), alginate; and poly(fumaric anhydride-co-sebacic anhydride (p[FA:SA]), copolymers of p[FA:SA], polyacrylates and polyacrylamides, and copolymers thereof, and combinations thereof. In some embodiments, the polymeric linker is preferably water-soluble.

For polymeric linkers, the number of monomers is typically greater than or equal to 1, such as 1-10 (e.g., oligomer) or greater than 10 (e.g., polymer), such as 10-1000 or greater.

iv. Reactive Moieties that React with Thiols

The binding agent contains at least two reactive moieties that react with thiols to form covalent bonds. The reactive moieties are capable of reacting with a thiol group in the hair or on the skin to form a stable covalent bond. The reactive moiety is typically an electrophilic moiety capable of forming a salt with the linker. Alternately, the reactive moiety can be a free radical forming moiety.

The binding agent contains at least two reactive moieties. However, the binding agent may contain three, four, five, six, or greater than six reactive moieties.

The reaction between the reactive moiety and the thiol groups may be initiated at room temperature and pressure when the reactive moiety contacts a thiol group in the hair or on the skin. In some embodiments, the reaction may require an initiator, such as heat, catalyst, basic conditions, or a free radical initiator. The rate of reaction between the reactive moiety and the thiol may be increased by changes in temperature, pH, and/or addition of one or more excipients, such as a catalyst; however, this is generally not required.

The two or more reactive moieties on the binding agent can be the same. In some embodiments, the two or more reactive moieties are different.

In some embodiments, the reactive moieties are capable of undergoing a conjugate additional reaction. The reactive moieties can independently be or contain a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinamide group, a sulfinamide group, a sulfonimidate group, or a sulfonimidamide group.

1. Michael Acceptor

A "Michael acceptor," as used herein, is a compound or moiety with at least one Michael acceptor functional group with the structure below:

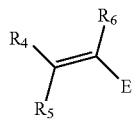

where E is —C(=O)R$_3$, —C(=O)OR$_3$, —C(=O)NHR$_3$, —CN, —S(O)R$_3$ or —S(O)$_2$R$^3$, where R$_3$, R$_4$, R$_5$, and R$_6$ taken independently, are hydrogen or a group or grouping selected from, but not limited to, alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, peptide, and polypeptide groups. In certain embodiments, R$_3$ and one of R$_4$, R$_5$, or R$_6$ may together form a ring.

Some suitable Michael acceptors include, but are not limited to molecules in which some or all of the structure above are residues of (meth)acrylic acid, fumaric acid, or maleic acid, substituted versions thereof, or combinations thereof, attached to the Michael acceptor molecule through an ester linkage.

The linker is attached to the Michael acceptor via R$_3$, R$_4$, R$_5$, or R$_6$. In some embodiments, R$_3$, R$_4$, R$_5$, or R$_6$ may be the linker.

2. Vinyl Sulfone

The chemistry of vinyl sulfones with respect to attack by nucleophiles is analogous to that of α,β-unsaturated ketones in that they can undergo a 1,4-type Michael addition without releasing any undesirable by-products.

3. Vinyl Sulfoximines

The chemistry of vinyl sulfoximines is similar to vinyl sulfones. The N-tosyl sulfoximine group is more electron withdrawing than the phenyl sulfone and therefore the vinyl groups will be more susceptible towards nucleophilic attack. N-substituents can be used to alter the electrophilic potential of the vinyl group.

4. Electrophilic Moiety Containing a Leaving Group

The reactive moiety may be an electrophile with a leaving group. Electrophile, as used herein refers to one or more functional groups or moieties that have an affinity for or attract electrons. Suitable electrophiles include, but are not limited to, ester moieties (—(CO)—O—R, wherein R is lower alkyl or the like), carbonyl moieties (—C(O)), carboxylic acid or carbonic acid (—COOH or —OCOOH), carbonate moieties (—O—(CO)—O—R, wherein R is lower alkyl or the like), urethane moieties (—O—(CO)—NH—R, wherein R is H, lower alkyl, or the like), substituted urethane moieties (—O—(CO)—NR'—R, where R' is a nonhydrogen substituent such as alkyl, aryl, alkaryl, or the like), amido moieties (—(CO)—NH—R, wherein R is H, lower alkyl, or the like), substituted amido moieties (—(CO)—NR'—R where R' is as defined previously), thioester moieties (—(CO)—S—R, wherein R is H, lower alkyl, or the like), sulfonic ester moieties (—S(O)$_2$—O—R, wherein R is H, lower alkyl, or the like), and the like. Other electrophiles will be known to those of ordinary skill in the art of organic chemistry and polymer science and/or can be readily found by reference to the pertinent texts and literature.

The electrophiles preferably contain a leaving group. Suitable leaving groups are well known in the art, see, e.g., "Advanced Organic Chemistry," Jerry March, 5th Ed., pp. 445-448, John Wiley and Sons, N.Y. Examples of leaving groups include, but are not limited to, halogen, sulfonyloxy, optionally substituted alkylsulfonyloxy, optionally substituted alkenylsulfonyloxy, optionally substituted arylsulfonyloxy. Specific examples of leaving groups include chloro, iodo, bromo, fluoro, methanesulfonyloxy (mesyloxy), tosyloxy, triflyloxy, nitrophenylsulfonyloxy (nosyloxy), bromophenylsulfonyloxy (brosyloxy), hydroxyl, carboxylate, carbonate, phosphate, phosphonate, phosphinate, phosphonium, urethane, urea, amide, imide, amine, ammonium, sulfonato, —N$_3$, CN, RO—, NH$_2$O—, NHRO—, N(R$^4$)$_2$O—, R$^4$CO$_2$—, R$^4$OCO$_2$—, R$^4$NCO$_2$—, R$^4$S—, R$^4$C(S)O—, R$^4$CS$_2$—, R$^4$SC(O)S—, R$^4$SCS$_2$— R$^4$SCO$_2$—, R$^4$OC(S)O—, R$^4$OCS$_2$—, R$^4$SO$_2$—, R$^4$SO$_3$—, R$^4$OSO$_2$—, R$^4$OSO$_3$—, R$^4$PO$_3$—, R$^4$OPO$_3$—, an N-imidazolyl group, an N-triazolyl group, an N-benzotriazolyl group, a benzotriazolyloxy group, an imidazolyloxy group, an N-imidazolinone group, an N-imidazolone group, an N-imidazolinethione group, an N-imidazolinethione group, an N-succinimidyl group, an N-phthalimidyl group, an N-succinimidyloxy group, an N-phthalimidyloxy group, —ON═C(CN)R$^4$, and a 2-pyridyloxy group. R$^4$ is preferably an alkyl group or an aryl group.

Preferably, the leaving group is removed from the reactive moieties and does not result in the formation of side product that disadvantageously affects the reaction between the reactive moieties and the thiol groups or form a material or compound that is unsuitable for contact with skin or hair.

In some embodiments, the leaving group is a halogen.

5. Electrophilic Thiol Acceptors

Electrophilic thiol acceptors, as used herein, refer to a chemical moiety that reacts with a thiol group so that the sulfur atom of the thiol group becomes covalently bonded to the thiol acceptor. Thiol acceptors are well known in the art. Koval (Reactions of Thiols, Russian Journal of Organic Chemistry, 2007, 43:319-349) discloses several electrophilic thiol acceptors, the disclosure of which is incorporated herein by reference.

Electrophilic thiol acceptors, in addition to those listed above, include but are not limited to an alpha-substituted acetyl group with the formula Y—CH$_2$—CO— wherein Y is a leaving group. Examples of leaving groups include, but are not limited to, chloride, bromide, iodide, mesylate, tosylate, and the like. If the thiol acceptor is an alpha-substituted acetyl group, the thiol adduct after covalent linkage to the acceptor forms the bond —S—CH$_2$—.

6. Free Radical-Forming Groups

The binding agent may contain at least two free radical-forming groups that can react with thiols. The free radical-forming groups on the binding agent can be the same. Alternately, the free radical-forming groups may be different. Suitable free radical forming groups include, but are not limited to acrylate groups, methacrylate groups, styrene groups, acryl amide groups, methacryl amide groups, maleate groups, fumarate groups, itaconate groups, vinyl ether groups, allyl ether groups, allyl ester groups, and vinyl ester groups. For example, suitable binding agents include ethylene glycol dimethacrylate, diethylene glycol diacrylate, allyl methacrylate, trimethylolpropane triacrylate, triallylamine, tetraallyloxyethane, and di- and triacrylates, mixed acrylates which, as well as acrylate groups, comprise further ethylenically unsaturated groups. Other examples of binding agents include N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives, pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. Other examples of binding agents include di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane, ethylene glycol dimethacrylate, diethylene glycol diacrylate, allyl methacrylate, trimethylolpropane triacrylate, triallylamine, tetraallyloxyethane, N,N'-methylenebisacrylamide, N,N'-methylenebismethacrylamide, butanediol diacrylate, butanediol dimethacrylate, trimethylolpropane triacrylate, triallyl cyanurate, diallyl maleate, a polyallyl ester, tetraallylethylenediamine, pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, di- and triacrylates of 3- to 15-tuply ethoxylated glycerol, di- and tri-acrylates of 3- to 15-tuply ethoxylated trimethylolpropane, and di- and tri-acrylates of 3- to 15-tuply ethoxylated trimethylolethane. As used herein, the term "tuply" refers to the number of monomeric units in the ethoxylated chain.

The reactive free radical moieties may require the presence of one or more initiators. Suitable initiators include, but are not limited to peroxides, hydroperoxides, hydrogen peroxide, persulfates, azo compounds, and redox initiators. Suitable organic peroxides include acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide, and tert-aryl perneodecanoate. Suitable azo compounds include 2,2'-azobisisobutyronitrile, 2,2'-azobis(2,4-dimethylvaleronitrile) and 2,2'-azobis(4-methoxy-2,4-dimethylvaleronitrile), preferably water-soluble azo initiators, such as, but not limited to, 2,2'-azobis{2-[1-(2-hydroxyethyl)-2-imidazolin-2-yl]propane}dihydrochloride, 2,2'-azobis-(2-amidinopropane) dihydrochloride, 2,2'-azobis[2-(2-imidazolin-2-yl)propane]dihydrochloride and 2,2'-azobis[2-(5-methyl-2-imidazolin-2-yl)propane]dihydrochloride. For the redox initiators, the oxidizing component is at least one of the peroxo compounds indicated above and the reducing component is, for example, ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide, or sodium hydroxymethylsulfoxylate.

In some embodiments, the molecule is:
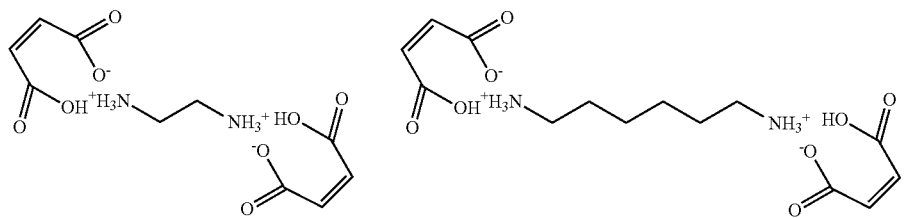
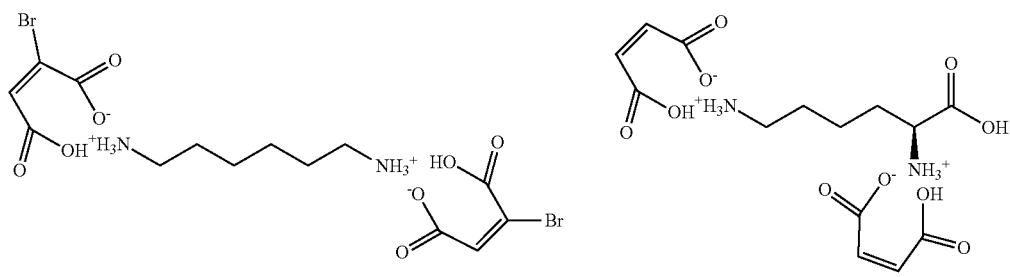
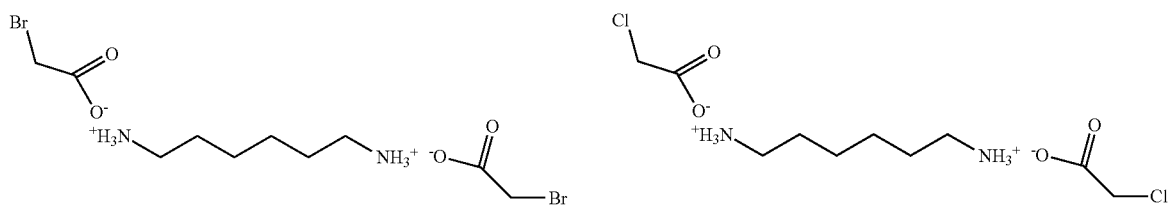
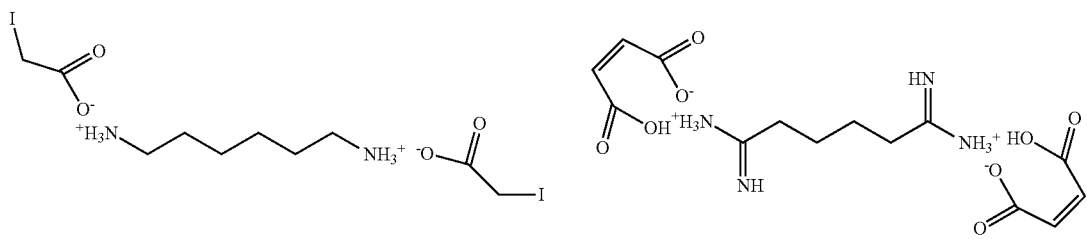
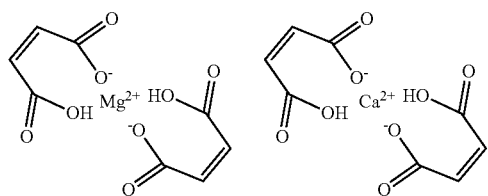
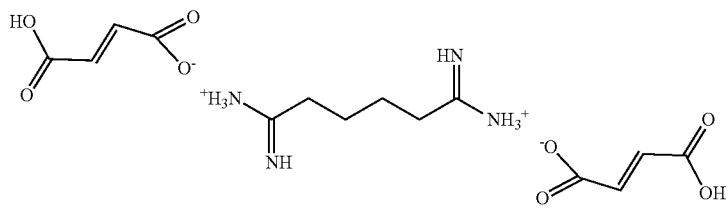
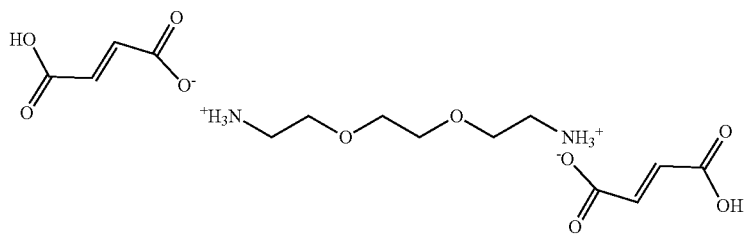
or

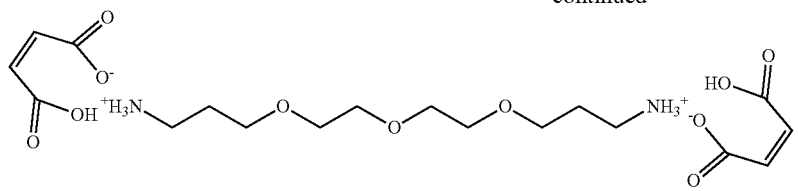
In some embodiments, the binding agent has the structure:
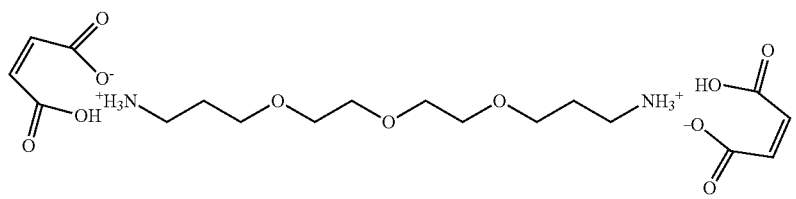
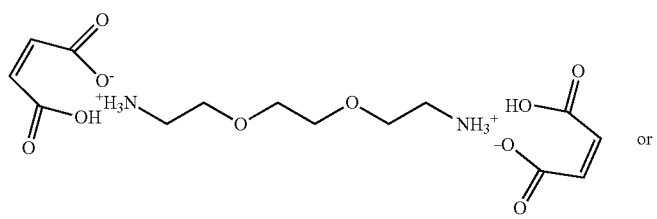 or
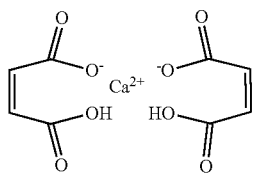
The reaction with thiol groups on hair follicles is as follows:
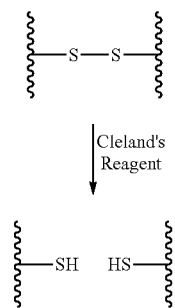

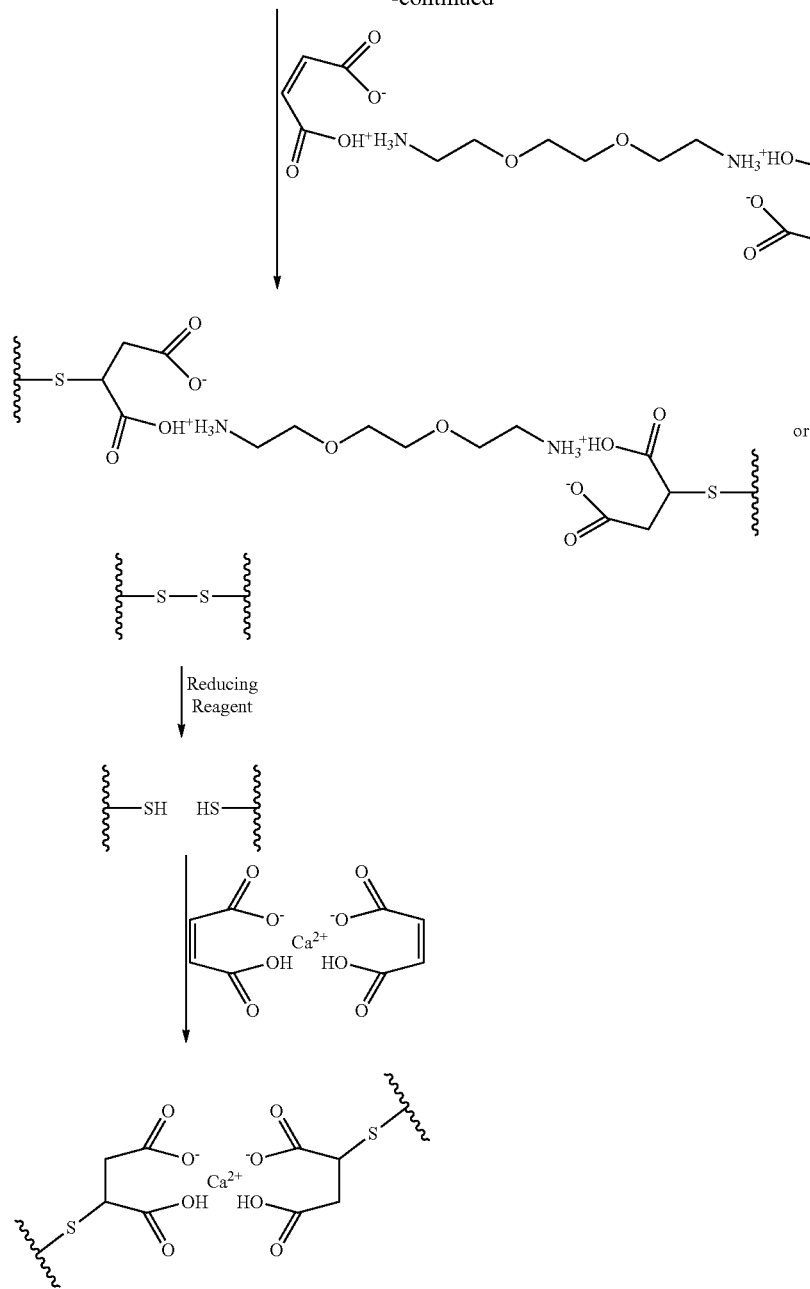

Other agents include, but are not limited to, acid-containing electrophiles, such as acrylic acid and bromo-acetic acid and similar compounds.

b. Excipients

The formulations typically contain one or more cosmetically acceptable excipients. Cosmetically acceptable excipients include, but are not limited to, water, preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

The formulations can contain at least two or more cosmetically acceptable excipients. In some forms, the formulations contain the binding agent, water, and optionally a preservative and/or fragrance.

The formulation for treating hair may be in any suitable physical form. Suitable forms include, but are not limited to low to moderate viscosity liquids, lotions, milks, mousses, sprays, gels, creams, shampoos, conditioners, and the like. Suitable excipients, such as those listed above, are included or excluded from the hair care formulation depending on the form of use of the formulation (e.g., hair spray, cream, conditioner, or shampoo).

The formulation for treating skin may be in any suitable physical form. Suitable forms include, but are not limited to low to moderate viscosity liquids, lotions, milks, mousses, sprays, gels, creams, ointments, and the like. Suitable excipients, such as those listed above, are included or excluded from the skin formulation depending on the form of use of the formulation (e.g., lotion, gel, ointment, or cream).

The pharmaceutical excipient is typically present in an amount ranging from about 10 wt % to about 99.99 wt % of the formulation, preferably about 40 wt % to about 99 wt %, more preferably from about 80 wt % to about to about 99 wt %.

i. Surfactants

Surfactants are surface-active agents that are able to reduce the surface tension of water and cause the formulation to slip across or onto the skin or hair. Surfactants also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond aminopropylamine oxide, aluminum hydrogenated tallow glutamate, aluminum lanolate, aminoethyl sulfate, aminopropyl lauryl glutamine, ammonium $C_{12-15}$ alkyl sulfate, ammonium $C_{12-15}$ pareth sulfate, ammonium $C_{12-16}$ alkyl sulfate, ammonium $C_{9-10}$ perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearyl gelatin/keratin amino acids/lysine hydroxypropyltrimonium chloride, amp-isostearyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, benzalkonium chloride, behenamide, behenamide, behenamidopropyl betaine, behenamide oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.1% to about 15% by weight of the formulation, preferably about 1% to about 10% by weight of the formulation.

ii. Emollients

Emollient refers to a material that protects against wetness or irritation, softens, soothes, coats, lubricates, moisturizes, protects, and/or cleanses the skin. Suitable emollients for use in the formulations include, but are not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or a combination thereof. More than one emollient may be included in the formulation.

The emollient is optionally included in an amount ranging from about 0.5% to about 15% by weight of the formulation, preferably from about 1% to about 10% by weight of the formulation.

iii. Emulsifiers

The formulations may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, or polysorbate-80, or combinations thereof. More than one emulsifier may be included in the formulation.

The emulsifier is optionally included in an amount ranging from about 0.05% to about 15% by weight of the formulation, preferably from about 0.1% to about 10% by weight of the formulation.

iv. Preservatives

One or more preservatives may be included in the formulations to prevent microbial growth in the formulations. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium—15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.1% to about 5% by weight of the formulation, preferably from about 0.3% to about 3% by weight of the formulation. Preferably, the formulations are paraben free.

v. Conditioning Agents

One or more conditioning agents may be included in the formulations. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl diimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) is optionally included in an amount ranging from about 0.1% to about 5% by weight of the formulation, preferably from about 0.3% to about 3% by weight of the formulation.

vi. Diluents

Diluent, as used herein, refers to a substance(s) that dilutes the binding agent. Water is the preferred diluent. The formulations typically contains greater than one percent (wt) water, preferably greater than five percent (wt) water, more preferably greater than 50% (wt) water, and most preferably greater than 80% (wt) water. Alcohols, such as ethyl alcohol and isopropyl alcohol, may be used at low concentrations (about 0.5% by weight of the formulation) to enhance hair or skin penetration and/or reduce odor.

vii. Viscosity Modifying Agents

The formulations may contain one or more viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

viii. Antioxidants

The formulations may contain one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexyldecyl ascorbate, superoxide dismutase, zinc, sodium metabisulfite, lycopene, ubiquinone, and combinations thereof.

ix. Opacifying Agents

The formulations may contain one or more opacifying agents. Opacifying agents are added to the formulations to make them opaque. Suitable opacifying agents include, but are not limited to, glycol distearate and ethoxylated fatty alcohols.

c. Forms of the Formulation i. Sprays

The formulation may be in the form of a spray. The spray typically includes the binding agent and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some embodiments, the formulation includes a surfactant. In some embodiments, the formulation contains water, fragrance, a preservative, and a binding agent. In some embodiments, the formulation contains water, fragrance, a preservative, and a binding agent. In some embodiments, the formulation contains water, a preservative, fragrance, the binding agent, and an anti-static agent. In some embodiments, the formulation contains water, a preservative, fragrance, the binding agent, and a hair conditioning agent. In some embodiments, the formulation contains water, a preservative, fragrance, the binding agent, and a surfactant.

The hair spray formulations may be dispensed from containers that include aerosol dispensers or pump spray dispensers. Such dispensers are known in the art and are commercially available from a variety of manufacturers.

1. Propellant

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The formulation may be in the form of a conditioner. The conditioner typically includes the binding agent in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

The binding agent may be included in any suitable concentration. Typical concentrations of the binding agent in the conditioner range from small such as approximately 0.01% (wt), preferably at least 0.1% (wt), to large amounts, such as up to 50% (wt). Preferably the conditioner contains the binding agent in a concentration ranging from 0.1% (wt) to 5% (wt), more preferably from 0.1% wt to 3%

(wt). While greater concentrations of binding agent could be present in the conditioner, they are generally not needed to achieve the desired results.

iii. Shampoos

The hair repair formulation may be in the form of a shampoo. The shampoo typically includes the binding agent in a suitable carrier. The binding agent may be included in any suitable concentration. Typical concentrations of the binding agent in the shampoo range from small amounts such as approximately 0.01% (wt), preferably at least 0.1% (wt), to large amounts, such as up to 50% (wt). Preferably the shampoo contains the binding agent in a concentration ranging from 0.1% (wt) to 5% (wt), more preferably from 0.1% wt to 3% (wt). While greater concentrations of binding agent could be present in the shampoo, they are generally not needed to achieve the desired results.

Additionally, the shampoo may include from about 0.5% to about 20% of a surfactant material. Surfactants utilized in shampoo compositions are well-known in the art and are disclosed, for example, in U.S. Pat. No. 6,706,258 to Gallagher et al. and U.S. Pat. No. 7,598,213 to Geary et al.

iv. Creams

The formulation may be in the form of a cream. The cream typically includes the binding agent in a suitable carrier. The binding agent may be included in any suitable concentration. Typical concentrations of the binding agent in the cream range from small amounts such as approximately 0.01% (wt), preferably at least 0.1% (wt), to large amounts, such as up to 50% (wt). Preferably the cream contains the binding agent in a concentration ranging from 0.1% (wt) to 5% (wt), more preferably from 0.1% wt to 3% (wt). While greater concentrations of binding agent could be present in the cream, they are generally not needed to achieve the desired results.

Additionally, the cream may include an oil, a hair conditioning agent, and/or a thickening agent. The cream may also include a fragrance, a plant extract, and/or a surfactant. The cream may be packaged in a tube, tub, bottle, or other suitable container.

v. Liquid Binding Formulations

In some embodiments, a liquid binding formulation is provided, which is mixed at the time of use with a second formulation, such as a coloring or highlighting formulation. In these embodiments, the liquid binding formulation may contain any suitable concentration of binding agent in a suitable carrier, typically a diluent, such as described above. The concentration of the binding agent is suitable to provide a mixture with the appropriate final volume and final concentration of binding agent.

For example, a liquid binding formulation can contain a concentration of binding agent ranging from about 5% (wt) to about 50% (wt) or greater. In a preferred embodiment, the liquid binding formulation contains about 20% (wt) binding agent.

The terms "highlighting" and "bleaching" are used synonymously herein. For highlighting applications, prior to use, a sufficient volume of a liquid binding formulation is mixed with a sufficient volume of a highlighting formulation to form a highlighting mixture having the desired concentration of binding agent. Typical concentrations of the binding agent in the highlighting mixture range from small amounts, such as approximately at least 0.01% (wt), preferably at least 0.1% (wt), to large amounts, such as up to 50% (wt). Preferably the highlighting mixture contains the binding agent in a concentration ranging from 0.1% (wt) to 5% (wt), more preferably from 0.1% wt to 3% (wt). While greater concentrations of binding agent could be present in the highlighting mixture, they are generally not needed to achieve the desired results.

Alternatively, two separate formulations are applied, such as a first formulation containing bleach (i.e. the highlighting formulation), and a second formulation containing a binding agent (i.e. the binding formulation) in an effective amount to covalently bind the free thiol groups. The highlighting formulation may be applied first, which produces free thiol groups in hair. Subsequently, the second binding formulation may be applied to bind the free thiol groups.

III. Kit

Kits for treating hair typically contain a binding formulation containing an effective amount of a binding agent to covalently bind latent free thiol groups in hair.

Instructions for use of the kit are also typically provided.

The kit may further contain a formulation, also referred to herein as the reducing formulation, capable of reducing the disulfide bonds in the hair and producing free thiol groups.

a. Reducing Formulation

The first formulation may be a reducing formulation. A reducing formulation contains a reducing agent capable of reducing the disulfide bonds in hair and producing free thiol groups. The reducing formulation may differ depending on the hair styling treatment desired (such as hair waving or hair straightening), the texture of the hair, the sensitivity of the user's skin, and the like.

Formulations containing reducing agents and their selection are well known to those skilled in the cosmetic industry. Suitable reducing agents include, but are not limited to, thioglycolic acid and thioglycolic acid salts and esters, thiolactic acid and thiolactic acid salts and esters, cysteine thioglycerol, thioglycolic hydrazide, thioglycolamide, glycerol monothioglycolate, sodium metabisulfite, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, polythiol derivatives formed by the addition of cysteamine onto a maleic anhydride-alkylvinylether copolymer, inorganic sulfites, inorganic bisulfites, cysteamine and its derivatives, dithioerythritol, organic phosphines, and Japanese relaxers.

In some embodiments, the kit contains a reducing formulation, which contains a reducing agent for permanent hair waving and hair curling such as acid perms, alkaline perms, perms having neutral pH, or perms using buffered alkaline waving lotions. Such reducing agents include, but are not limited to thioglycolic acid and its derivative salts and esters, thiolactic acid and its derivative salts and esters, cysteine and its derivatives, cysteamine and its derivatives, inorganic sulfites, and inorganic bisulfites such as sodium metabisulfite, dithiothreitol, dithioerythritol, organic phosphines, and Japanese relaxers.

In other embodiments, the kit contains a reducing formulation, which contains a reducing agent for straightening hair. Such reducing agents include, but are not limited, to inorganic bisulfites such as sodium metabisulfite, inorganic sulfites, ammonium thioglycolate, dithiothreitol, dithioerythritol, organic phosphines, and Japanese relaxers.

The amount of the reducing agent in the reducing formulation is sufficient to rupture a sufficient number of disulfide bonds for effective hair waving, hair curling, or hair straightening as would be appreciated by one of skill in the art.

b. Coloring Formulation

The first formulation may be a coloring treatment. The first formulation may be formulated as two or more components that may be mixed together before application to the hair. For example, the first formulation may be in the form of two components such as a dye precursor and an oxidant. Typically, the hair coloring formulation contains a reducing agent capable of reducing the disulfide bonds in hair and producing free thiol groups. Suitable reducing agents include, but are not limited to, thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols and hydroquinone. The amount of the reducing agent in the first formulation is sufficient to rupture a sufficient number of disulfide bonds for effective diffusion of the hair coloring ingredients as would be appreciated by one of skill in the art.

The components of the first formulation may differ depending on the hair coloring treatment desired (such as for semi-permanent, demi-permanent, or permanent hair color), the texture of the hair, the sensitivity of the user's skin, and such the like. Hair coloring formulations for different hair coloring treatment, hair texture, and hair sensitivity are known to those of skill in the art.

c. Binding Formulation

The binding formulation contains an effective amount of a binding agent to bind free thiols in the hair. Suitable formulations containing the binding agents are discussed above. The binding formulation may be in any suitable form. Suitable forms include, but are not limited to, low to moderate viscosity liquids, lotions, milks, mousses, sprays, gels, creams, shampoos, conditioners, and the like. The binding formulation will be present in a suitable container, which depends on the form of the formulation.

In one embodiment, the binding formulation is provided as two or more separate ingredients. For example, the binding agent may be provided as a dry powder in a sealed package and the excipient provided in a vial or other container. A suitable mixing container for the binding agent and the excipient may be provided.

Optionally, the binding agent is premixed with a shampoo or conditioner.

In some embodiments, the binding formulation (or second formulation) is mixed with the first formulation (reducing formulation or hair coloring treatment), and the mixture is applied to the hair.

d. Other Materials in the Kit

The kit optionally contains shampoos and conditioners. Suitable shampoos and conditioners include, but are not limited to LiQWd® Hydrating Shampoo and LiQWd® Hydrating Conditioner.

The kit may further contain an odor eliminator. The odor eliminator can be incorporated into the reducing formulation. Alternately, the odor eliminator is present in a suitable container for use before or after washing the binding formulation from the hair. Some suitable odor eliminators are known to those of ordinary skill in the art.

IV. Methods of Use

The methods disclosed herein are concerned with treating hair with free thiol groups.

a. Treating Damaged Hair with Free Thiol Groups

In one embodiment, prior to treatment with a binding agent, the hair has been damaged and the thiol groups in the hair are free thiols. The binding agent can be applied to the hair to bind the free thiol groups. Preferably, the binding agent is applied at least within one week of the hair being damaged, preferably within three days, more preferably within two days, most preferably, the same day.

i. Rinse or Wash the Hair

Optionally, the hair may be shampooed and/or conditioned prior to applying the binding formulation. Alternately, the hair may only be rinsed with water prior to application of the binding formulation.

ii. Apply the Binding Formulation to the Hair

Subsequent to shampooing, conditioning, and/or rinsing the hair, the binding formulation is applied to the hair. Alternately, the hair does not have to be washed or rinsed prior to application of the binding formulation. In this embodiment, the binding formulation is applied to dry hair.

The binding formulations may be used as a daily conditioning treatment for hair.

Typically, the amount of binding formulation applied is sufficient to saturate the hair.

The binding formulation may be applied to the hair as a single application, or application of the binding agent may be repeated one or more times. Typically, the amount of binding formulation applied in each application is sufficient to saturate the hair. The volume of binding formulation applied to the hair in each application may be about 1 to about 100 mL per person depending on their length and volume of hair. In some embodiments, application of the binding agent could be repeated immediately (e.g. within about 10 to 15 seconds) or between about one and five minutes, greater than five minutes, between about five and ten minutes, greater than ten minutes, between about ten and twenty (20) minutes after the first application.

iii. Remove the Binding Formulation from the Hair

Preferably, the hair is washed or rinsed subsequent to the application of the binding formulation. The hair may be rinsed and subsequently washed immediately (e.g. within 10, 15, 25, 30, 45, 60 seconds (one minute), two minutes, three minutes, four, or five minutes following application) after final application of the binding agent. Alternatively the hair may be rinsed and washed within about 30 minutes following application, preferably between about 5 minutes and about 20 minutes, more preferably about 10 minutes after the final application of the binding agent to the hair, depending on the hair type.

Alternately, the hair does not have to be washed or rinsed subsequent to application of the binding formulation.

The binding agent covalently binds latent free thiols in the hair. The thiols remain bound for at least one week, preferably for at least one month following application of the binding agent. The thiols may remain bound for longer periods of time, such as for about two months or more following application of the binding agent. The binding reaction is a stable reaction, such that the thiols may remain bound even if subjected to a hair coloring treatment (simultaneous or subsequent to the binding reaction).

b. Chemical Treatment of Hair with a Reducing Agent

In one embodiment, prior to treatment with a binding agent, the hair has been subjected to a reducing agent used for waving (also referred to herein as hair perming or permanent waves), curling, and/or straightening of the hair.

i. Apply a Reducing Agent to the Hair

The first step in waving, curling, or straightening hair is breaking the cysteine disulfide bonds to form free thiol moieties. The process for breaking the cysteine disulfide bonds is via application of a reducing agent. The process for applying the reducing agent involves following normal perming or hair straightening procedures, that are known to those skilled in the art. For example, to perm a hair, the hair is first washed and set on perm rods of various sizes. Second, a reducing agent, such as thioglycolate reducing solution or lotion, is applied to the hair. The hair is allowed to set for a specified period of time, and then the thioglycolate solution is rinsed from the hair.

The application of hydrogen peroxide in this process is optional. In some processes, such as when treating previously chemically treated hair, hydrogen peroxide is generally not used. In other processes, such as when perming virgin hair, hydrogen peroxide may be added. In these embodiments, hydrogen peroxide is typically added after the reducing agent is rinsed out. Then the hydrogen peroxide is rinsed from the hair prior to adding the binding agent.

ii. Apply the Binding Agent

Subsequent to the reducing treatment, one or more of the binding agent, or a formulation thereof is applied to the hair. Although the binding agent is typically applied on the same day as treatment with the reducing agent, it may be applied later, such as within 1 to 2 weeks following treatment with the reducing agent.

Typically, the amount of binding formulation applied is sufficient to saturate the hair. The binding agent is generally rinsed and shampooed from the hair after the desired level of hair waving, curling, or straightening is achieved. In some embodiments, the binding agent is rinsed from the hair immediately (e.g. within 10, 15, 25, 30, 45, or 60 seconds following application) following the final application of the binding agent. Alternatively the hair may be rinsed and washed about within about 30 minutes following application, preferably between about 5 minutes and about 20 minutes, more preferably about 10 minutes after the final application of the binding agent to the hair, depending on the hair type. The binding agent can be rinsed from the hair within 10, 15, 25, 30, 45, or 60 seconds from the hair after application, and still achieve a desired level of hair waving, curling, or straightening.

The binding agent may be applied to the hair as a single application, or application of the binding agent may be repeated one or more times. Typically, the amount of binding formulation applied in each application is sufficient to saturate the hair. In some embodiments, the volume of binding formulation applied to the hair in each application is about 1 to about 10 mL per perm rod. In some embodiments, application of the binding agent could be repeated immediately (e.g. within 10 to 15 seconds) or approximately 1, 5, 7.5, 10, 12.5, 15, 17.5, or 20 minutes after the first application. In some embodiments, the second application is about 7 minutes to about 10 minutes after the first application.

The binding agent is rinsed from the hair after its application. The hair may be rinsed and washed immediately (e.g. within 10 to 15 seconds following application) after final application of the binding agent. Alternatively the hair may be rinsed and washed about 10 minutes or later after the final application of the binding agent, such as about 15 minutes to about 30 minutes, preferably about 20 minutes after repeated application of the binding agent to the hair.

The binding agent covalently binds the free thiols in the hair. The thiols remain bound for at least one week, two weeks, three weeks, four weeks, one month, two months or more.

The binding agents are generally washed from the individual's hair on the same day as they are applied. In contrast, traditional perms which use only hydrogen peroxide (and do not involve the addition of a cross-linking agent) are generally not washed for at least 48 hours following application (washing the hair prior to 48 hours following a traditional permanent treatment may result in significant loss in the amount of curl in the hair and/or cause damage to the hair).

The compositions described herein improve hair quality, such as appearance (e.g., sheen) and feel, increase dry strength (e.g., tensile strength), and decrease hair breakage when the hair is subjected to subsequent treatments, such as coloring.

In some embodiments, hair breakage decreases by 5, 10, 15, 20, 25, 30, 35, 40, 45, 50, 55, 60, 65, 70, or 75% or higher after treatment with the binding agent compared to untreated hair from the same individual. Hair breakage is a significant problem encountered during coloring and other treatments.

c. Apply the Coloring Formulation to the Hair

The coloring formulation is generally applied to an individual's hair following normal hair coloring procedures that are known to those skilled in the art. Typically, hair color treatments include two complementary processes: bleaching the hair's natural pigment and/or other artificial pigments present in the hair, and diffusion of dye precursors into the hair, followed by coupling reactions that result in the formation of chromophores within the hair shaft, which are too large to diffuse out of the hair. The hair coloring formulation may be a highlighting formulation, such as formed by mixing bleach powder and developer. More complex colors may contain several precursors and many couplers, and may involve multiple reactions.

The dye precursors may contain several ingredients, each with different functions. The first ingredient is usually an alkalizing agent (usually ammonia and/or an ammonia substitute, such as monoethanolamine [MEA]). The alkalizing agent serves a number of roles in the hair colorant process including swelling the hair fiber to aid in diffusion of the dye precursors. The dye precursors generally include p-diamines and p-aminophenols. Precursors are oxidized to active intermediates once they have penetrated the hair shaft. Intermediates then react with color couplers to create wash resistant dyes. More specifically, the intermediates, in the presence of an oxidant, couple with another oxidation dye intermediate molecule to form a large fused ring color compound within the hair shaft. The precursor intermediate should penetrate the hair shaft prior to the coupling reaction since the fused ring product is too large to penetrate the hair shaft. Couplers modify the color produced by the oxidation of precursor compounds. The primary difference between demi-permanent and permanent products is the alkalizing agent and the concentration of peroxide. The cuticle does not swell as greatly with demi-permanent dyes, making dye penetration less efficient compared to permanent coloring products.

Several coloring formulations use a reducing agent, such as sodium bisulfate, to break disulfide bonds in the hair, allowing deeper penetration of the hair coloring dyes into the hair. Specifically, the method includes reducing some of the disulfide linkages of the cysteine in the hair shafts to thiol groups while breaking hydrogen bonds. The reducing process changes the chemical and cosmetic characteristics of the hair, which are undesirable.

The hair dyeing process may be followed by a shampoo and conditioning treatment, a neutralizing rinse or an acid balanced shampoo containing in addition to cationic or amphoteric surfactants, cation-active emollients and quaternary polymers. Alternately, the hair dyeing process may be followed by application of the binding formulations described herein, before a shampoo and/or conditioning treatment.

i. Applying Binding Formulation

The binding formulation may be applied simultaneously with the hair coloring formulation or subsequently to the application of the hair coloring formulation. For example, the binding formulation may be mixed with the hair coloring treatment and the mixture, containing both the binding formulation and the hair coloring treatment, may be applied to the hair.

Alternatively, subsequent to coloring the hair, the binding formulation, or a formulation thereof is applied to the hair. Although the binding agent is typically applied on the same day as the coloring treatment, it may be applied later such as within 1 to 2 weeks following treatment with the reducing agent. Typically, the amount of binding formulation (or a mixture of the binding formulation and the hair coloring formulation) applied is enough to saturate the hair. The binding formulation may be applied to the hair as a single application, or application of the binding agent may be repeated one or more times. Typically, the amount of binding formulation applied in each application is sufficient to saturate the hair. The volume of binding formulation applied to the hair in each application may be about 1 to about 100 mL per person depending on their length and volume of hair. In some embodiments, application of the binding agent could be repeated immediately (e.g. within 10 to 15 seconds) or approximately 1, 5, 7.5, 10, 12.5, 15, 17.5, or 20 minutes after the first application.

The binding agent can be rinsed and shampooed from the hair immediately following application, for example within 10, 15, 25, 30, 45, or 60 seconds, or two, three, four, or five minutes after application. Alternatively, the binding agent may be rinsed from the hair within about 30 minutes following application, preferably between about 5 minutes and about 20 minutes, more preferably about 10 minutes after application of the binding agent to the hair, depending on hair type.

If the binding formulation is combined with the hair coloring treatment and applied as a mixture to the hair, then the mixture remains on the hair as long as needed for the hair coloring treatment. Typically the mixture is applied for approximately 10 minutes. The mixture is removed from the hair in accordance with standard methods for hair coloring treatments, e.g., rinse and shampoo, approximately 10 minutes after applying the mixture.

The binding formulation is rinsed from the hair after its application. The hair may be rinsed and subsequently washed immediately (e.g. within 10 to 15 seconds following application) after final application of the binding agent. Preferably, the hair is rinsed and/or washed about 10 minutes or later after the final application of the binding agent, such as about 15 minutes to about 30 minutes, optionally about 20 minutes after repeated application of the binding agent to the hair.

The binding agent covalently binds the free thiols in the hair. The thiols remain bound for at least one week, two weeks, three weeks, four weeks, one month, or two months, or more.

The binding agents are generally washed from the individual's hair on the same day as they are applied. In contrast, traditional perms which use only hydrogen peroxide (and do not involve the addition of a cross-linking agent) are generally not washed for at least 48 hours following application (washing the hair prior to 48 hours following a traditional permanent treatment may result in significant loss in the amount of curl in the hair and/or cause damage to the hair).

The compositions described herein improve hair quality, such as appearance (e.g., sheen) and feel, increase dry strength (e.g., tensile strength), and decrease hair breakage when the hair is subjected to subsequent treatments, such as coloring.

In some embodiments, hair breakage decreases by 5, 10, 15, 20, 25, 30, 35, 40, 45, 50, 55, 60, 65, 70, 75, 80, 85, or 90% or higher after treatment with the binding agent compared to untreated hair from the same individual. Hair breakage is a significant problem encountered during coloring and other treatments.

EXAMPLES

I. Example 1: Comparison of Traditional Perm Versus Perm Using Bismaleate Binding Agent a. General Hair samples were obtained from a human subject and cut in ½ inch wide wefts.

Reducing agents: Ammonium thioglycolate (ATG) was obtained from a permanent wave kit manufactured by Zotos. 300 mg of Dithiothreitol in a 10 g solution was also used as the reducing agent.

Binding formulation: A bismaleate binding agent 2,2'-(ethane-1,2-diylbis(oxy))bis(ethan-1-amine)di-maleate at a concentration of 300 mg in 10 g total solution (water) was used.

b. Methods i. Method for Perming Hair Using the Binding Agents

The hair was washed with clarifying shampoo, towel dried, and then rolled around a perm rod. Ammonium thioglycolate or dithiothreitol was then applied to the hair and left on the hair for 10 minutes to 1 hour. The hair was then rinsed for 30 seconds to 1 minute and then blotted dry with a towel.

The binding formulation was applied to the hair, via a needle nose applicator, drenching the hair. The binding agent was left on the hair for a period of about 7.5 minutes. The hair was drenched for a second time with the binding formulation and left for a second 7.5 minutes, for a total of 15 minutes. The hair was then rinsed with water for about 1-2 minutes then unrolled from the perm rods. After the hair was removed from the perm rods, the hair was shampooed and conditioned with various salon shampoo and conditioner brands, including LiQWd® Hydrating Shampoo and Hydrating Conditioner. The washing and drying steps were repeated 40 times.

A second portion of hair was permed as described above, except, hydrogen peroxide was used instead of the binding formulation.

c. Results

Both perms (utilizing the binding formulation or hydrogen peroxide) showed only slight reduction in the overall curl after 40 cycles of washing and drying with the same shampoo and conditioner. However, the appearance and texture of the perm using the binding formulation showed more sheen and less frizz compared to the perm using hydrogen peroxide.

II. Example 2: Comparison of Hair Breakage Due to Repeated Application of Traditional Perm and the Binding Formulations a. Methods Two hair samples were obtained. Both samples were treated with dithiothreitol or ammonium thioglycolate as described in Example 1. One of the hair samples was subsequently treated with the binding formulation, while the other was neutralized with hydrogen peroxide. The process was completed the same day for the hair treated with the binding formulation. The process was completed in three days with hydrogen peroxide (traditional perm).

The procedure was repeated three times for each hair sample over a 48 hour time period.

b. Results

Upon visual inspections, the second hair sample treated with the binding formulation showed little or no signs of breakage. However, the first hair sample treated with hydrogen peroxide showed significant breakage.

III. Example 3: Comparison of the Extent of Damage to Hair Previously Relaxed with a Japanese Relaxer a. Methods Two samples of hair, the first previously straightened with a Japanese relaxer (Yuko), and the second previously straightened with a no lye relaxer (African Pride Miracle Deep Conditioning) were obtained. The samples were treated as described in Examples 1 and 2 using the binding formulation.

Another hair sample, previously straightened with a no lye relaxer (African Pride Miracle Deep Conditioning) was obtained. The sample was treated with a traditional hair straightening perm (Zotos).

b. Results

The hair samples treated with the binding formulation showed no noticeable damage. However, the sample treated with a traditional perm showed significant breaking, even during application.

IV. Example 4: Hair Sheen and Texture after Treatment with Binding Formulation a. General A sample of untreated virgin gray hair was obtained from a human subject.

Binding formulation: The bismaleate binding agent in Example 1 (300 mg) was dissolved in water (10 g). The resulting solution was mixed with LiQWD Volumizing Conditioner® in a 1:1 ratio.

b. Methods

A section of the virgin gray hair was washed with LiQWD® Hydrating Shampoo and then blotted dry with a towel. The hair was then combed with a wide tooth comb followed by combing with a fine tooth comb for 2 minutes.

After combing, the binding formulation (about 4 mL) was applied to the hair sample by hand and then the sample combed through for approximately 1 minute. The hair sample was left undisturbed for a period of about 10 minutes, after which it was rinsed with water, and then washed with LiQWD® Volumizing Shampoo and Conditioner before being examined.

The hair sample was washed and conditioned for an additional five (5) times with LiQWD® Volumizing Shampoo and Conditioner.

A second section of the virgin gray hair, the control, was treated identically as above, except the binding formulation was not applied to the control hair sample. Thus after the hair was combed, LiQWD Volumizing Conditioner® (without a binding agent) was applied to the hair sample by hand.

c. Results:

The hair sample treated with the binding formulation had more shine and felt softer to the touch than the original untreated sample. The treated hair sample gave an overall healthier appearance compared to the control sample.

The shine, texture, and overall appearance remained intact after five shampoo and conditioning treatments.

V. Example 5: Hair Sheen and Texture after Treatment with Binding Formulation a. General A sample of untreated virgin blonde hair described as highly porous and difficult to comb through was obtained from a human subject.

Binding formulation: The bismaleate binding agent in Example 1 (300 mg) was dissolved in water (10 g). The resulting solution was mixed with LiQWD Enhancing Conditioner® in a 1:1 ratio.

b. Methods

A section of the virgin blonde hair was washed with LiQWD® Hydrating Shampoo and then blotted dry with a towel. The hair was then combed with a wide tooth comb followed by combing with a fine tooth comb for 5 minutes.

The binding formulation (about 7 mL) was then applied to the hair sample by hand and the sample combed through for approximately 2 minutes. The hair sample was left undisturbed for a period of about 5 minutes after which the hair was treated again with the binding formulation (about 4 mL). The hair sample was combed through for approximately 10 seconds and left undisturbed for about 5 minutes.

The hair sample was then rinsed with water then washed with LiQWD® Sulfate Free Enhancing Shampoo and Conditioner before examination.

Following initial examination, the sample was washed and conditioned for an additional two (2) times with LiQWD® Sulfate Free Enhancing Shampoo and Conditioner.

A second section of the virgin blonde hair, the control, was treated identically as above, except the binding formulation was not applied to the control hair sample. Thus, after the hair was combed, LiQWD Volumizing Conditioner® (without a binding agent) was applied to the hair sample by hand.

c. Results

The hair sample treated with the binding formulation had more shine and felt softer to the touch than the original untreated sample. The treated hair sample gave an overall healthier appearance compared to the control sample.

The shine, texture, and overall appearance remained intact after two shampoo and conditioning treatments.

VI. Example 6: Color Retention and Texture of Colored Hair Treated with the Binding Formulation a. General Three hair samples were obtained from a human subject and cut in ½ inch wide wefts.

Coloring formulation: The permanent hair coloring formulation was obtained from a L'Oreal® permanent hair coloring service (L'Oreal® Majirel permanent color #10 with 20 volume peroxide).

Binding formulation: A bismaleate binding agent, 2,2'-(ethane-1,2-diylbis(oxy))bis(ethan-1-amine)di-maleate, at a concentration of 300 mg in 10 g total solution (water) was used.

b. Methods

The hair samples were washed with a clarifying shampoo then towel dried. The samples were then colored with the L'Oreal® permanent hair color service, which was left on the hair samples for approximately 35-40 minutes.

The first color treated hair sample ("control") was subsequently rinsed and washed with Liqwd® Hydrating Shampoo and Conditioner five times before being photographed.

The binding formulation was applied to the second and third color treated hair samples via a spray bottle and massaging using the fingers. The binding formulation was left on the second hair sample for a period of about 1 minute and on the third sample for a period of about 10 minutes. The hair samples were subsequently rinsed, and then washed with Liqwd® Hydrating Shampoo and Conditioner five times before being examined.

c. Results

The hair samples treated with the binding formulation showed better color retention, more shine, and less frizz than the control. The hair samples treated with the binding formulation felt smoother to the touch and combined with the lower frizz and added sheen gave an overall healthier appearance over the control.

VII. Example 7: Comparison of Color Retention in Traditionally Permed Hair and Hair Permed Using the Binding Formulations a. Method A ½ inch wide weft of hair sample, obtained from a human subject, was washed with clarifying shampoo then towel dried. Ammonium thioglycolate or dithiothreitol was mechanically pulled through the hair with a wide and a fine toothcomb several times then left on the hair for 10 minutes to 1 hour. The hair was then rinsed for 30 seconds to 1 minute with water, and then towel dried.

The binding formulation, described in Example 1, was then applied via a needle nose applicator drenching the hair and leaving it on for 7.5 minutes. This step was repeated, for a total of 15 minutes. The hair was then rinsed for 1-2 minutes, shampooed, and then conditioned with various salon shampoo and conditioner brands, including LiQWd® Hydrating Shampoo and Hydrating Conditioner.

A second sample of hair was straightened, as described above, but using hydrogen peroxide instead of the binding formulation. The hair samples were washed and conditioned repeatedly.

i. Comparison of Hair Color

After both hair samples were washed five times using LiQWd® Hydrating Shampoo and LiQWd® Hydrating Conditioner, the samples were examined for their color retention.

b. Results

The hair sample treated with the binding formulation displayed a color closer in intensity to the hair sample prior to the first washing, compared to the hair treated with hydrogen peroxide.

VIII. Example 8: Comparison of Hair Treated with Highlighting Formulation Applied Simultaneously with Binding Formulation and Hair Treated with Highlighting Formulation Alone The binding formulation in Example 1 contained the bismaleate binding agent at concentrations of 2400 mg in 10 g total solution (water).

Two swatches of human hair were tested. A sample was taken from the same head, 1 inch wide, and split in half. The color was medium brown and had been previously color treated with an unknown professional hair color.

Swatch 1, ½ inch wide and 8 inches long, was lightened with traditional highlighting ingredients mixed with a binding formulation. 1 oz of Joico Verocolor Veroxide developer-20 volume was mixed with 1 oz Joico Verolight powder bleach to form the highlighting formulation. Then 9 mL of the binding formulation was added to the highlighting formulation to form a mixture.

The mixture was applied on the Swatch 1 hair with an applicator brush as the hair lay on aluminum foil. The foil was then wrapped around the swatch and allowed to process for 35 minutes. The swatch was rinsed and shampooed one time.

Swatch 2, the control, ½ inch wide and 8 inches long, was lightened with traditional highlighting ingredients in the absence of a binding formulation. 1 oz of Joico Verocolor Veroxide developer-20 volume was mixed with 1 oz Joico Verolight powder bleach to form a highlighting formulation with a creamy consistency.

The highlighting formulation was applied on the Swatch 2 hair with an applicator brush as the hair lay on aluminum foil. The foil was then wrapped around the swatch and allowed to process for 35 minutes. The swatch was rinsed and shampooed one time.

a. Results

A noticeable difference in hair quality between Swatch 1 and Swatch 2 was observed. Swatch 1 hair was softer, less frizzy, appeared hydrated, with more shine than the control, Swatch 2.

Both swatches were washed and conditioned 5 more times with the same noticeable benefits of Swatch 1 (treated with the mixture of highlighting formulation and binding formulation) compared to the control, Swatch 2 (treated with highlighting formulation, alone).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating keratin of a person, the method comprising contacting the keratin with a composition comprising a compound having a chemical structure of:

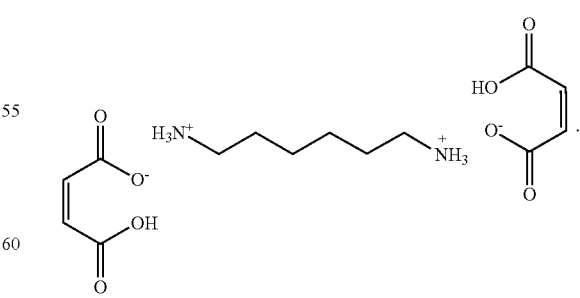

2. The method of claim 1, wherein the composition further comprises water and an alcohol.

3. The method of claim 2, wherein the composition comprises greater than 1 wt. % water.

4. The method of claim 2, wherein the alcohol comprises ethyl alcohol.

5. The method of claim 1, wherein the composition is in the form of a shampoo.

6. The method of claim 1, wherein the composition is in the form of a conditioner.

7. The method of claim 1, wherein the composition is in the form of a gel.

8. The method of claim 1, wherein the composition is in the form of a cream.

9. The method of claim 1, wherein the composition is in the form of a liquid.

10. The method of claim 1, wherein the composition further comprises a cosmetically acceptable excipient comprising a surfactant, a vitamin, a preservative, an antioxidant, an emollient, or a pH adjusting agent, or any combination thereof.

11. The method of claim 1, wherein the compound binds to a free thiol in the keratin.

12. The method of claim 1, wherein the compound binds to the keratin through a covalent bond.

13. The method of claim 1, wherein the keratin is comprised in the person's hair and the composition is applied to the person's hair.

14. The method of claim 1, wherein the keratin is comprised in the person's skin and the composition is applied to the person's skin.

15. The method of claim 1, wherein the composition comprises 0.01 wt. % to 25 wt. % of the compound.

16. The method of claim 1, wherein the composition consists of the compound, water, and an alcohol.

17. The method of claim 1, wherein the composition has a pH of 5 to 8.

* * * * *